United States Patent
Kinney et al.

(10) Patent No.: US 11,191,832 B2
(45) Date of Patent: Dec. 7, 2021

(54) MONITORING IMMUNOTHERAPY OF LEWY BODY DISEASE FROM CONSTIPATION SYMPTOMS

(71) Applicant: PROTHENA BIOSCIENCES LIMITED, Dublin (IE)

(72) Inventors: Gene G. Kinney, Burlingame, CA (US); Theresa Anne Neumann, Menlo Park, CA (US); Daniel Keith Ness, San Mateo, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 539 days.

(21) Appl. No.: 15/037,978

(22) PCT Filed: Nov. 19, 2014

(86) PCT No.: PCT/IB2014/066141
§ 371 (c)(1),
(2) Date: May 19, 2016

(87) PCT Pub. No.: WO2015/075635
PCT Pub. Date: May 28, 2015

(65) Prior Publication Data
US 2016/0279238 A1 Sep. 29, 2016

Related U.S. Application Data

(60) Provisional application No. 61/906,372, filed on Nov. 19, 2013.

(51) Int. Cl.
*A61K 39/395* (2006.01)
*C07K 16/18* (2006.01)
*G01N 33/68* (2006.01)
*A61B 5/00* (2006.01)

(52) U.S. Cl.
CPC ........ *A61K 39/3955* (2013.01); *A61B 5/4848* (2013.01); *C07K 16/18* (2013.01); *G01N 33/6896* (2013.01); *C07K 2317/24* (2013.01); *C07K 2317/34* (2013.01); *C07K 2317/56* (2013.01); *C07K 2317/565* (2013.01); *G01N 2800/2814* (2013.01); *G01N 2800/2835* (2013.01)

(58) Field of Classification Search
None
See application file for complete search history.

(56) References Cited

U.S. PATENT DOCUMENTS

| | | | |
|---|---|---|---|
| 8,092,801 B2 * | 1/2012 | Schenk | A61K 39/0007 424/133.1 |
| 2010/0278814 A1 | 11/2010 | Schenk et al. | |
| 2012/0142902 A1 | 6/2012 | Schenk et al. | |
| 2013/0108546 A1 * | 5/2013 | Saldanha | C07K 16/18 424/1.49 |
| 2016/0279238 A1 | 9/2016 | Neumann et al. | |

FOREIGN PATENT DOCUMENTS

| | | |
|---|---|---|
| WO | WO 2005/013889 A2 | 2/2005 |
| WO | WO 2005/047860 A2 | 5/2005 |
| WO | WO 2006/020581 A2 | 2/2006 |
| WO | WO 2013/0635166 A1 | 5/2013 |
| WO | WO 2015/075635 A2 | 5/2015 |

OTHER PUBLICATIONS

PCT/IB2014/066141 Invitation to Pay Additional Fees and, Where Applicable, Protest Fee dated Mar. 3, 2015.
PCT/IB2014/066141 International Search and Written Opinion dated Jun. 19, 2015.
Abbott, et al., "Bowel Movement Frequency in Late-Life and Incidental Lew Bodies," *Movement Disorders*, vol. 22, No. 11, pp. 1581-1586, (2007).
Masliah, et al., "Passive Immunization Reduces Behavioral and Neuropathological Deficits in an Alpha-Synuclein Transgenic Model of Lew Body Disease," *PLoS ONE*, vol. 6, Issue 4, pp. 1-17, (Apr. 2011).
Poewe, "Non-motor symptoms in Parkinson's disease," *European Journal of Neurology*, 15(Suppl.1):14-20, (2008).
PCT/IB2014/066141 Preliminary Report on Patentability dated Jun. 2, 2016.
Jankovic et al., "Safety and Tolerability of Multiple Ascending Doses of PRX002/RG7935, an Anti-α-Synuclein Monoclonal Antibody, in Patients With Parkinson Disease, a Randomized Clinical Trial," JAMA Neurol., 9 pages, doi:10.1001/jamaneurol.2018.1487, (2018). [Retrieved from the Internet Aug. 13, 2018: <URL: https://jamanetwork.com/journals/jamaneurology/fullarticle/2685097>].
Saito, et al., "Neuropathology," *Clin Neurol*, 51:1168-1171, (2011). English Abstract.
Lebouvier, et al., "Colonic Biopsies to Assess the Neuropathology of Parkinson's Disease and Its Relationship with Symptoms," *PLoS one*, vol. 5, Issue 9, e12728, (Sep. 2010).

* cited by examiner

*Primary Examiner* — Adam Weidner
(74) *Attorney, Agent, or Firm* — Alston & Bird LLP

(57) ABSTRACT

The invention provides methods of monitoring immunotherapy directed against alpha-synuclein by comparing a subject's constipation symptoms before treatment and at one or more times during and/or after treatment. The immunotherapeutic regime can be monitored depending on the results of treatment.

27 Claims, No Drawings
Specification includes a Sequence Listing.

SEQUENCE LISTING

<160> NUMBER OF SEQ ID NOS: 129

<210> SEQ ID NO 1
<211> LENGTH: 113
<212> TYPE: PRT
<213> ORGANISM: Artificial Sequence
<220> FEATURE:
<223> OTHER INFORMATION: Synthesized

<400> SEQUENCE: 1

Asp Ile Val Met Ser Gln Ser Pro Ser Leu Ala Val Ser Val Gly
1               5                   10                  15

Glu Lys Val Thr Met Ser Cys Lys Ser Ile Gln Thr Leu Leu Tyr Ser
                20                  25                  30

Ser Asn Gln Lys Asn Tyr Leu Ala Trp Phe Gln Lys Pro Gly Gln
            35                  40                  45

Ser Pro Lys Leu Leu Ile Tyr Trp Ala Ser Ile Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 2
<211> LENGTH: 107
<212> TYPE: PRT
<213> ORGANISM: Artificial Sequence
<220> FEATURE:
<223> OTHER INFORMATION: Synthesized

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys
            100                 105

<210> SEQ ID NO 3
<211> LENGTH: 113
<212> TYPE: PRT
<213> ORGANISM: Artificial Sequence
<220> FEATURE:
<223> OTHER INFORMATION: Synthesized

<400> SEQUENCE: 3

Asp Ile Gln Met Thr Gln Ser Pro Ser Ser Leu Ser Ala Ser Val Gly
1               5                   10                  15

-continued

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 4
<211> LENGTH: 113
<212> TYPE: PRT
<213> ORGANISM: Artificial Sequence
<220> FEATURE:
<223> OTHER INFORMATION: Synthesized

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 5
<211> LENGTH: 113
<212> TYPE: PRT
<213> ORGANISM: Artificial Sequence
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln

```
                   85                  90                  95
Tyr Tyr Ser Tyr Pro Leu Thr Phe Gly Gly Gly Thr Lys Leu Glu Ile
                100                 105                 110

Lys

<210> SEQ ID NO 6
<211> LENGTH: 116
<212> TYPE: PRT
<213> ORGANISM: Artificial Sequence
<220> FEATURE:
<223> OTHER INFORMATION: Synthesized

<400> SEQUENCE: 6

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
                20                  25                  30

Gly Met Ser Trp Val Arg Gln Thr Ser Asp Lys Arg Leu Glu Trp Val
            35                  40                  45

Ala Ser Ile Ser Ser Gly Gly Ser Thr Tyr Tyr Pro Asp Asn Val
        50                  55                  60

Lys Gly Arg Phe Thr Ile Ser Arg Glu Asp Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ser Arg Gly Gly Ala Gly Ile Asp Tyr Trp Gly Gln Gly Thr Thr Leu
                100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthesized

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ser Asp Met Asp Tyr Trp Gly Gln Gly Thr Leu Val
                100                 105                 110

Thr Val Ser Ser
        115

<210> SEQ ID NO 8
<211> LENGTH: 116
<212> TYPE: PRT
```

<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Ala Gly Ile Asp Tyr Trp Gly Gln Gly Thr Leu Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthesized

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Ala Gly Ile Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Synthesized

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
 50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
                100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthesized

<400> SEQUENCE: 11

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
                100                 105                 110

Thr Val Ser Ser
        115

<210> SEQ ID NO 12
<211> LENGTH: 140
<212> TYPE: PRT
<213> ORGANISM: Homo sapiens

<400> SEQUENCE: 12

Met Asp Val Phe Met Lys Gly Leu Ser Lys Ala Lys Glu Gly Val Val
 1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 324
<212> TYPE: DNA
<213> ORGANISM: Artificial Sequence
<220> FEATURE:
<223> OTHER INFORMATION: Synthesized

<400> SEQUENCE: 14
cgaaactgtg gctgcaccat ctgtcttcat cttcccgcca tctgatgagc agttgaaatc      60
tggaactgcc tctgttgtgt gcctgctgaa taacttctat cccagagagg ccaaagtaca     120
gtggaaggtg gataacgccc tccaatcggg taactcccag gagagtgtca cagagcagga     180
cagcaaggac agcacctaca gcctcagcag caccctgacg ctgagcaaag cagactacga     240
gaaacacaaa gtctacgcct gcgaagtcac ccatcagggc ctgagctcgc ccgtcacaaa     300
gagctcaaca ggggagagtg ttag                                            324

<210> SEQ ID NO 15
<211> LENGTH: 330
<212> TYPE: PRT
<213> ORGANISM: Artificial Sequence
<220> FEATURE:
<223> OTHER INFORMATION: Synthesized

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

|      |      |      |      |      | 35  |      |      |      |      | 40  |      |      |      |      | 45  |      |
|------|------|------|------|------|-----|------|------|------|------|-----|------|------|------|------|-----|------|

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 991
<212> TYPE: DNA
<213> ORGANISM: Artificial Sequence
<220> FEATURE:
<223> OTHER INFORMATION: Synthesized

<400> SEQUENCE: 16

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
acatctgcaa cgtgaatcac aagcccagca acaccaaggt ggacaagaga gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
```

```
aggtcacatg cgtggtggtg gacgtgagcc acgaagaccc tgaggtcaag ttcaactggt      480
acgtggacgg cgtggaggtg cataatgtca agacaaagcc gcgggaggag cagtacaaca      540
gcacgtaccg tgtggtcagc gtcctcaccg tcctgcacca ggactggctg aatggcaagg      600
agtacaagtg caaggtctcc aacaaagccc tcccagcccc catcgagaaa accatctcca      660
aagccaaagg gcagccccga gaaccacagg tgtacacgct gcccccatcc cgggaggaga      720
tgaccaagaa ccaggtcagc ctgacctgcc tggtcaaagg cttctatccc agcgacatcg      780 ccgtggagtgg gagagcaatg ggcagccgga gaacaactac aagaccacgc ctcccgtgct      840
ggactccgac ggctccttct tcctctatag caagctcacc gtggacaaga gcaggtggca      900 gcagggaac gtcttctcat gctccgtgat gcatgaggct ctgcacaacc actacacgca       960
gaagagcctc tccctgtccc cgggtaaatg a                                     991
```

<210> SEQ ID NO 17
<211> LENGTH: 339
<212> TYPE: DNA
<213> ORGANISM: Artificial Sequence
<220> FEATURE:
<223> OTHER INFORMATION: Synthesized

<400> SEQUENCE: 17

```
gacatccaga tgacccagtc cccctcctcc ctgtccgcct ccgtgggcga ccgcgtgacc       60
atcacctgca gtccatcca gaccctgctg tactcctcca accagaagaa ctacctggcc      120
tggttccagc agaagcccgg caaggccccc aagctgctga tctactgggc ctccatccgc     180
aagtccggcg tgccctcccg cttctccggc tccggctccg gcaccgactt caccctgacc     240
atctcctccc tgcagcccga ggacttcgcc acctactact gccagcagta ctactcctac     300
cccctgacct cggcggcgg caccaagctg gagatcaag                             339
```

<210> SEQ ID NO 18
<211> LENGTH: 339
<212> TYPE: DNA
<213> ORGANISM: Artificial Sequence
<220> FEATURE:
<223> OTHER INFORMATION: Synthesized

<400> SEQUENCE: 18

```
gacatccaga tgacccagtc cccctcctcc ctgtccgcct ccgtgggcga ccgcgtgacc       60
atcacctgca gtccatcca gaccctgctg tactcctcca accagaagaa ctacctggcc      120
tggtaccagc agaagcccgg caaggccccc aagctgctga tctactgggc ctccatccgc     180
aagtccggcg tgccctcccg cttctccggc tccggctccg gcaccgactt caccctgacc     240
atctcctccc tgcagcccga ggacttcgcc acctactact gccagcagta ctactcctac     300
cccctgacct cggcggcgg caccaagctg gagatcaag                             339
```

<210> SEQ ID NO 19
<211> LENGTH: 339
<212> TYPE: DNA
<213> ORGANISM: Artificial Sequence
<220> FEATURE:
<223> OTHER INFORMATION: Synthesized

<400> SEQUENCE: 19

```
gacatccaga tgacccagtc cccctcctcc ctgtccgcct ccgtgggcga ccgcgtgacc       60
atcacctgca gtccatcca gaccctgctg tactcctcca accagaagaa ctacctggcc      120
```

```
tggttccagc agaagcccgg caaggccccc aagctgctga tctactgggc ctccatccgc    180
aagtccggcg tgccctcccg cttctccggc tccggctccg gcaccgactt caccctgacc    240
atctcctccc tgcagcccga ggacctggcc acctactact gccagcagta ctactcctac    300
cccctgacct tcggcggcgg caccaagctg gagatcaag                          339
```

<210> SEQ ID NO 20
<211> LENGTH: 348
<212> TYPE: DNA
<213> ORGANISM: Artificial Sequence
<220> FEATURE:
<223> OTHER INFORMATION: Synthesized

<400> SEQUENCE: 20

```
gaggtgcagc tggtggagtc cggcggcggc ctggtgcagc ccggcggctc cctgcgcctg     60
tcctgcgccg cctccggctt caccttctcc aactacggca tgtcctgggt gcgccaggcc    120
cccggcaagg gcctggagtg ggtggcctcc atctcctccg gcggcggctc cacctactac    180
cccgacaacg tgaagggccg cttcaccatc tcccgcgacg acgccaagaa ctccctgtac    240
ctgcagatga actccctgcg cgccgaggac accgccgtgt actactgctc ccgcggcggc    300
gccggcatcg actactgggg ccagggcacc ctggtgaccg tgtcctcc                 348
```

<210> SEQ ID NO 21
<211> LENGTH: 348
<212> TYPE: DNA
<213> ORGANISM: Artificial Sequence
<220> FEATURE:
<223> OTHER INFORMATION: Synthesized

<400> SEQUENCE: 21

```
gaggtgcagc tggtggagtc cggcggcggc ctggtgcagc ccggcggctc cctgcgcctg     60
tcctgcgccg cctccggctt caccttctcc aactacggca tgtcctgggt gcgccaggcc    120
cccggcaagg gcctggagtg ggtggcctcc atctcctccg gcggcggctc cacctactac    180
cccgacaacg tgaagggccg cttcaccatc tcccgcgaca acgccaagaa ctccctgtac    240
ctgcagatga actccctgcg cgccgaggac accgccgtgt actactgctc ccgcggcggc    300
gccggcatcg actactgggg ccagggcacc ctggtgaccg tgtcctcc                 348
```

<210> SEQ ID NO 22
<211> LENGTH: 348
<212> TYPE: DNA
<213> ORGANISM: Artificial Sequence
<220> FEATURE:
<223> OTHER INFORMATION: Synthesized

<400> SEQUENCE: 22

```
gaggtgcagc tggtggagtc cggcggcggc ctggtgcagc ccggcggctc cctgcgcctg     60
tcctgcgccg cctccggctt caccttctcc aactacggca tgtcctgggt gcgccaggcc    120
cccggcaagg gcctggagtg ggtggcctcc atctcctccg gcggcggctc cacctactac    180
cccgacaacg tgaagggccg cttcaccatc tcccgcgacg acgccaagaa ctccctgtac    240
ctgcagatga actccctgcg cgccgaggac accgccgtgt actactgcgc ccgcggcggc    300
gccggcatcg actactgggg ccagggcacc ctggtgaccg tgtcctcc                 348
```

<210> SEQ ID NO 23
<211> LENGTH: 348
<212> TYPE: DNA
<213> ORGANISM: Artificial Sequence

```
<220> FEATURE:
<223> OTHER INFORMATION: Synthesized

<400> SEQUENCE: 23
gaggtgcagc tggtggagtc cggcggcggc ctggtgcagc ccggcggctc cctgcgcctg      60
tcctgcgccg cctccggctt caccttctcc aactacggca tgtcctgggt cgcgcaggcc     120
cccggcaagg gcctggagtg ggtggcctcc atctcctccg gcggcggctc cacctactac     180
cccgacaacg tgaagggccg cttcaccatc tcccgcgaca cgccaagaa ctccctgtac      240 ctgcagatga actccctgcg cgccgaggac accgccgtgt actactgcgc cgcggcggc      300 gccggcatcg actactgggg ccagggcacc ctggtgaccg tgtcctcc                  348

<210> SEQ ID NO 24
<211> LENGTH: 22
<212> TYPE: PRT
<213> ORGANISM: Artificial Sequence
<220> FEATURE:
<223> OTHER INFORMATION: Synthesized

<400> SEQUENCE: 24

Met Asp Met Arg Val Pro Ala Gln Leu Leu Gly Leu Leu Met Leu Trp
1               5                   10                  15

Val Ser Gly Ser Ser Gly
            20

<210> SEQ ID NO 25
<211> LENGTH: 66
<212> TYPE: DNA
<213> ORGANISM: Artificial Sequence
<220> FEATURE:
<223> OTHER INFORMATION: Synthesized

<400> SEQUENCE: 25
atggacatgc gcgtgcccgc ccagctgctg ggcctgctga tgctgtgggt gtccggctcc      60
tccggc                                                                66

<210> SEQ ID NO 26
<211> LENGTH: 19
<212> TYPE: PRT
<213> ORGANISM: Artificial Sequence
<220> FEATURE:
<223> OTHER INFORMATION: Synthesized

<400> SEQUENCE: 26

Met Glu Phe Gly Leu Ser Trp Leu Phe Leu Val Ala Ile Leu Lys Gly
1               5                   10                  15

Val Gln Cys

<210> SEQ ID NO 27
<211> LENGTH: 57
<212> TYPE: DNA
<213> ORGANISM: Artificial Sequence
<220> FEATURE:
<223> OTHER INFORMATION: Synthesized

<400> SEQUENCE: 27
atggagttcg gcctgtcctg gctgttcctg gtggccatcc tgaagggcgt gcagtgc         57

<210> SEQ ID NO 28
<211> LENGTH: 113
<212> TYPE: PRT
<213> ORGANISM: Artificial Sequence
```

```
<220> FEATURE:
<223> OTHER INFORMATION: Synthesized
<220> FEATURE:
<221> NAME/KEY: VARIANT
<222> LOCATION: 42
<223> OTHER INFORMATION: Xaa = Y or F
<220> FEATURE:
<221> NAME/KEY: VARIANT
<222> LOCATION: 89
<223> OTHER INFORMATION: Xaa = F or L

<400> SEQUENCE: 28
```

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Xaa Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Xaa Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

```
<210> SEQ ID NO 29
<211> LENGTH: 116
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 74
<223> OTHER INFORMATION: Xaa = N or D
<220> FEATURE:
<221> NAME/KEY: VARIANT
<222> LOCATION: 97
<223> OTHER INFORMATION: Xaa = A or S

<400> SEQUENCE: 29
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Xaa Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Xaa Arg Gly Gly Ala Gly Ile Asp Tyr Trp Gly Gln Gly Thr Leu Val
            100                 105                 110

Thr Val Ser Ser
        115

<210> SEQ ID NO 30
<211> LENGTH: 106
<212> TYPE: PRT
<213> ORGANISM: Artificial Sequence
<220> FEATURE:
<223> OTHER INFORMATION: Synthesized

<400> SEQUENCE: 30

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 31
<211> LENGTH: 321
<212> TYPE: DNA
<213> ORGANISM: Artificial Sequence
<220> FEATURE:
<223> OTHER INFORMATION: Synthesized

<400> SEQUENCE: 31

```
aactgtggct gcaccatctg tcttcatctt cccgccatct gatgagcagt tgaaatctgg      60
aactgcctct gttgtgtgcc tgctgaataa cttctatccc agagaggcca agtacagtg     120 gaaggtggat aacgccctcc aatcgggtaa ctcccaggag agtgtcacag agcaggacag     180
caaggacagc acctacagcc tcagcagcac cctgacgctg agcaaagcag actacgagaa     240
acacaaagtc tacgcctgcg aagtcaccca tcagggcctg agctcgcccg tcacaaagag     300
ctcaacaggg gagagtgtta g                                               321
```

<210> SEQ ID NO 32
<211> LENGTH: 220
<212> TYPE: PRT
<213> ORGANISM: Artificial Sequence
<220> FEATURE:
<223> OTHER INFORMATION: Synthesized

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95
```

Tyr Tyr Ser Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 33
<211> LENGTH: 219
<212> TYPE: PRT
<213> ORGANISM: Artificial Sequence
<220> FEATURE:
<223> OTHER INFORMATION: Synthesized

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 34

<211> LENGTH: 446
<212> TYPE: PRT
<213> ORGANISM: Artificial Sequence
<220> FEATURE:
<223> OTHER INFORMATION: Synthesized

<400> SEQUENCE: 34

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Val Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
            435                 440                 445

<210> SEQ ID NO 35
<211> LENGTH: 330
<212> TYPE: PRT
<213> ORGANISM: Artificial Sequence
<220> FEATURE:
<223> OTHER INFORMATION: Synthesized

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 446
<212> TYPE: PRT
<213> ORGANISM: Artificial Sequence
<220> FEATURE:
<223> OTHER INFORMATION: Synthesized

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Val Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 37
<211> LENGTH: 446
<212> TYPE: PRT
<213> ORGANISM: Artificial Sequence
<220> FEATURE:
<223> OTHER INFORMATION: Synthesized

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 38
<211> LENGTH: 345
<212> TYPE: DNA
<213> ORGANISM: Artificial Sequence
<220> FEATURE:
<223> OTHER INFORMATION: Synthesized

<400> SEQUENCE: 38
caggtccagc tgcagcagtc tggggctgaa ctggcaaaac ctggggacctc agtgcagatg      60 tcctgcaagg cttctggcta caccttact aattactgga tgaactggat aaaagcgagg     120
cctggacagg gtctggaatg gattggggct actaatccta acaatggtta tactgactac     180
aatcagaggt tcaaggacaa ggccatatta actgcagaca atcctccaa tacagcctac     240 atgcacctga gcagcctgac atctgaagac tctgcagtct atttctgtgc aagtgggggg     300
cacttggctt actggggcca ggggactgtg gtcactgtct ctgca                     345

<210> SEQ ID NO 39
<211> LENGTH: 115
<212> TYPE: PRT
<213> ORGANISM: Artificial Sequence
<220> FEATURE:
<223> OTHER INFORMATION: Synthesized

<400> SEQUENCE: 39

Gln Val Gln Leu Gln Gln Ser Gly Ala Glu Leu Ala Lys Pro Gly Thr
1               5                   10                  15

Ser Val Gln Met Ser Cys Lys Ala Ser Gly Tyr Thr Phe Thr Asn Tyr
                20                  25                  30

Trp Met Asn Trp Ile Lys Ala Arg Pro Gly Gln Gly Leu Glu Trp Ile
            35                  40                  45

Gly Ala Thr Asn Pro Asn Asn Gly Tyr Thr Asp Tyr Asn Gln Arg Phe

```
                  50                  55                  60
Lys Asp Lys Ala Ile Leu Thr Ala Asp Lys Ser Ser Asn Thr Ala Tyr
 65                  70                  75                  80

Met His Leu Ser Ser Leu Thr Ser Glu Asp Ser Ala Val Tyr Phe Cys
                 85                  90                  95

Ala Ser Gly Gly His Leu Ala Tyr Trp Gly Gln Gly Thr Val Val Thr
            100                 105                 110

Val Ser Ala
        115
```

<210> SEQ ID NO 40
<211> LENGTH: 57
<212> TYPE: DNA
<213> ORGANISM: Artificial Sequence
<220> FEATURE:
<223> OTHER INFORMATION: Synthesized

<400> SEQUENCE: 40

```
atggaaaggc actggatctt tctcttcctg ttatcagtaa ctggaggtgt ccactcc       57
```

<210> SEQ ID NO 41
<211> LENGTH: 19
<212> TYPE: PRT
<213> ORGANISM: Artificial Sequence
<220> FEATURE:
<223> OTHER INFORMATION: Synthesized

<400> SEQUENCE: 41

```
Met Glu Arg His Trp Ile Phe Leu Phe Leu Leu Ser Val Thr Gly Gly
 1               5                  10                  15

Val His Ser
```

<210> SEQ ID NO 42
<211> LENGTH: 336
<212> TYPE: DNA
<213> ORGANISM: Artificial Sequence
<220> FEATURE:
<223> OTHER INFORMATION: Synthesized

<400> SEQUENCE: 42

```
gatgttgtga tgacccaaat tccactctac ctgtctgtca gtcctggaga tcaagcctcc      60
atctcttgca gatctagtca gagccttttc catagtaaag aaacaccta tttacattgg     120 tatctgcaga agccaggcca gtctccaaag ctcctgatca cagggtttc aaccgattt      180 tctggggtcc cagacaggtt cagtggcagt ggatcaggga cagatttcac actcaagatc     240
agcggagtgg aggctgaaga tctgggagtt tatttctgtt ctcaaagtgc acatgttccg     300
tggacgttcg gtggaggcac caagctggaa atcaga                              336
```

<210> SEQ ID NO 43
<211> LENGTH: 112
<212> TYPE: PRT
<213> ORGANISM: Artificial Sequence
<220> FEATURE:
<223> OTHER INFORMATION: Synthesized

<400> SEQUENCE: 43

```
Asp Val Val Met Thr Gln Ile Pro Leu Tyr Leu Ser Val Ser Pro Gly
 1               5                  10                  15

Asp Gln Ala Ser Ile Ser Cys Arg Ser Ser Gln Ser Leu Phe His Ser
             20                  25                  30
```

```
            Lys Gly Asn Thr Tyr Leu His Trp Tyr Leu Gln Lys Pro Gly Gln Ser
                         35                  40                  45

Pro Lys Leu Leu Ile Asn Arg Val Ser Asn Arg Phe Ser Gly Val Pro
             50                  55                  60

Asp Arg Phe Ser Gly Ser Gly Ser Gly Thr Asp Phe Thr Leu Lys Ile
             65                  70                  75                  80

Ser Gly Val Glu Ala Glu Asp Leu Gly Val Tyr Phe Cys Ser Gln Ser
                             85                  90                  95

Ala His Val Pro Trp Thr Phe Gly Gly Gly Thr Lys Leu Glu Ile Arg
                        100                 105                 110

<210> SEQ ID NO 44
<211> LENGTH: 60
<212> TYPE: DNA
<213> ORGANISM: Artificial Sequence
<220> FEATURE:
<223> OTHER INFORMATION: Synthesized

<400> SEQUENCE: 44
atgaagttgc ctgttaggct gttggtgctg atgttctgga ttcctgcttc cagcagtgat        60

<210> SEQ ID NO 45
<211> LENGTH: 20
<212> TYPE: PRT
<213> ORGANISM: Artificial Sequence
<220> FEATURE:
<223> OTHER INFORMATION: Synthesized

<400> SEQUENCE: 45

Met Lys Leu Pro Val Arg Leu Leu Val Leu Met Phe Trp Ile Pro Ala
 1               5                  10                  15

Ser Ser Ser Asp
            20

<210> SEQ ID NO 46
<211> LENGTH: 12
<212> TYPE: PRT
<213> ORGANISM: Artificial Sequence
<220> FEATURE:
<223> OTHER INFORMATION: Synthesized

<400> SEQUENCE: 46

Val Asp Pro Asp Asn Glu Ala Tyr Glu Gly Gly Cys
 1               5                  10

<210> SEQ ID NO 47
<211> LENGTH: 5
<212> TYPE: PRT
<213> ORGANISM: Artificial Sequence
<220> FEATURE:
<223> OTHER INFORMATION: Synthesized

<400> SEQUENCE: 47

Asn Tyr Trp Met Asn
 1               5

<210> SEQ ID NO 48
<211> LENGTH: 17
<212> TYPE: PRT
<213> ORGANISM: Artificial Sequence
<220> FEATURE:
<223> OTHER INFORMATION: Synthesized

<400> SEQUENCE: 48
```

Ala Thr Asn Pro Asn Asn Gly Tyr Thr Asp Tyr Asn Gln Arg Phe Lys
1               5                   10                  15

Asp

<210> SEQ ID NO 49
<211> LENGTH: 6
<212> TYPE: PRT
<213> ORGANISM: Artificial Sequence
<220> FEATURE:
<223> OTHER INFORMATION: Synthesized

<400> SEQUENCE: 49

Gly Gly His Leu Ala Tyr
1               5

<210> SEQ ID NO 50
<211> LENGTH: 16
<212> TYPE: PRT
<213> ORGANISM: Artificial Sequence
<220> FEATURE:
<223> OTHER INFORMATION: Synthesized

<400> SEQUENCE: 50

Arg Ser Ser Gln Ser Leu Phe His Ser Lys Gly Asn Thr Tyr Leu His
1               5                   10                  15

<210> SEQ ID NO 51
<211> LENGTH: 7
<212> TYPE: PRT
<213> ORGANISM: Artificial Sequence
<220> FEATURE:
<223> OTHER INFORMATION: Synthesized

<400> SEQUENCE: 51

Arg Val Ser Asn Arg Phe Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized

<400> SEQUENCE: 52

Ser Gln Ser Ala His Val Pro Trp Thr
1               5

<210> SEQ ID NO 53
<211> LENGTH: 402
<212> TYPE: DNA
<213> ORGANISM: Artificial Sequence
<220> FEATURE:
<223> OTHER INFORMATION: Synthesized

<400> SEQUENCE: 53
atggaaaggc actggatctt tctcttcctg ttatcagtaa ctggaggtgt ccactcccag      60
gtccagctgc agcagtctgg ggctgaactg gcaaaacctg gacctcagt gcagatgtcc     120 tgcaaggctt ctggctacac ctttactaat tactggatga actggataaa agcgaggcct    180
ggacagggtc tggaatggat tgggctact aatcctaaca atggttatac tgactacaat    240
cagaggttca aggacaaggc catattaact gcagacaaat cctccaatac agcctacatg    300
cacctgagca gcctgacatc tgaagactct gcagtctatt tctgtgcaag tggggggcac    360
ttggcttact ggggccaggg gactgtggtc actgtctctg ca        402

<210> SEQ ID NO 54
<211> LENGTH: 134
<212> TYPE: PRT
<213> ORGANISM: Artificial Sequence
<220> FEATURE:
<223> OTHER INFORMATION: Synthesized

<400> SEQUENCE: 54

Met Glu Arg His Trp Ile Phe Leu Phe Leu Leu Ser Val Thr Gly Gly
1               5                   10                  15

Val His Ser Gln Val Gln Leu Gln Gln Ser Gly Ala Glu Leu Ala Lys
            20                  25                  30

Pro Gly Thr Ser Val Gln Met Ser Cys Lys Ala Ser Gly Tyr Thr Phe
        35                  40                  45

Thr Asn Tyr Trp Met Asn Trp Ile Lys Ala Arg Pro Gly Gln Gly Leu
    50                  55                  60

Glu Trp Ile Gly Ala Thr Asn Pro Asn Asn Gly Tyr Thr Asp Tyr Asn
65                  70                  75                  80

Gln Arg Phe Lys Asp Lys Ala Ile Leu Thr Ala Asp Lys Ser Ser Asn
                85                  90                  95

Thr Ala Tyr Met His Leu Ser Ser Leu Thr Ser Glu Asp Ser Ala Val
            100                 105                 110

Tyr Phe Cys Ala Ser Gly Gly His Leu Ala Tyr Trp Gly Gln Gly Thr
        115                 120                 125

Val Val Thr Val Ser Ala
    130

<210> SEQ ID NO 55
<211> LENGTH: 393
<212> TYPE: DNA
<213> ORGANISM: Artificial Sequence
<220> FEATURE:
<223> OTHER INFORMATION: Synthesized

<400> SEQUENCE: 55
atgaagttgc ctgttaggct gttggtgctg atgttctgga ttcctgcttc cagcagtgat        60
gttgtgatga cccaaattcc actctacctg tctgtcagtc ctggagatca agcctccatc       120
tcttgcagat ctagtcagag ccttttccat agtaaaggaa acacctattt acattggtat       180
ctgcagaagc caggccagtc tccaaagctc ctgatcaaca gggtttccaa ccgattttct       240
ggggtcccag acaggttcag tggcagtgga tcagggacag atttcacact caagatcagc       300
ggagtggagg ctgaagatct gggagtttat ttctgttctc aaagtgcaca tgttccgtgg       360
acgttcggtg aggcaccaa gctggaaatc aga                                    393

<210> SEQ ID NO 56
<211> LENGTH: 131
<212> TYPE: PRT
<213> ORGANISM: Artificial Sequence
<220> FEATURE:
<223> OTHER INFORMATION: Synthesized

<400> SEQUENCE: 56

Met Lys Leu Pro Val Arg Leu Leu Val Leu Met Phe Trp Ile Pro Ala
1               5                   10                  15

Ser Ser Ser Asp Val Val Met Thr Gln Ile Pro Leu Tyr Leu Ser Val
            20                  25                  30

Ser Pro Gly Asp Gln Ala Ser Ile Ser Cys Arg Ser Ser Gln Ser Leu
            35                  40                  45

Phe His Ser Lys Gly Asn Thr Tyr Leu His Trp Tyr Leu Gln Lys Pro
    50                  55                  60

Gly Gln Ser Pro Lys Leu Leu Ile Asn Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Gly Val Glu Ala Glu Asp Leu Gly Val Tyr Phe Cys
            100                 105                 110

Ser Gln Ser Ala His Val Pro Trp Thr Phe Gly Gly Gly Thr Lys Leu
        115                 120                 125

Glu Ile Arg
    130

<210> SEQ ID NO 57
<211> LENGTH: 118
<212> TYPE: PRT
<213> ORGANISM: Artificial Sequence
<220> FEATURE:
<223> OTHER INFORMATION: Synthesized

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
                20                  25                  30

Ala Ile Asn Trp Val Arg Gln Ala Pro Gly Gln Gly Leu Glu Trp Met
            35                  40                  45

Gly Gly Ile Ile Pro Ile Phe Gly Thr Thr Thr Tyr Ala Gln Lys Phe
        50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asn Leu Asn Trp Leu Asp Pro Trp Gly Gln Gly Thr
            100                 105                 110

Leu Val Thr Val Ser Ser
        115

<210> SEQ ID NO 58
<211> LENGTH: 115
<212> TYPE: PRT
<213> ORGANISM: Artificial Sequence
<220> FEATURE:
<223> OTHER INFORMATION: Synthesized

<400> SEQUENCE: 58

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
                20                  25                  30

Trp Met Asn Trp Val Arg Gln Ala Pro Gly Gln Gly Leu Glu Trp Ile
            35                  40                  45

Gly Ala Thr Asn Pro Asn Asn Gly Tyr Thr Asp Tyr Asn Gln Arg Phe
        50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly His Leu Ala Tyr Trp Gly Gln Gly Thr Leu Val Thr
            100                 105                 110

Val Ser Ser
        115

<210> SEQ ID NO 59
<211> LENGTH: 115
<212> TYPE: PRT
<213> ORGANISM: Artificial Sequence
<220> FEATURE:
<223> OTHER INFORMATION: Synthesized

<400> SEQUENCE: 59

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly His Leu Ala Tyr Trp Gly Gln Gly Thr Leu Val Thr
            100                 105                 110

Val Ser Ser
        115

<210> SEQ ID NO 60
<211> LENGTH: 115
<212> TYPE: PRT
<213> ORGANISM: Artificial Sequence
<220> FEATURE:
<223> OTHER INFORMATION: Synthesized

<400> SEQUENCE: 60

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Ser Gly Gly His Leu Ala Tyr Trp Gly Gln Gly Thr Leu Val Thr
            100                 105                 110

Val Ser Ser
        115

<210> SEQ ID NO 61
<211> LENGTH: 115
<212> TYPE: PRT
<213> ORGANISM: Artificial Sequence
<220> FEATURE:
<223> OTHER INFORMATION: Synthesized

<400> SEQUENCE: 61

```
Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
                20                  25                  30

Trp Met Asn Trp Val Arg Gln Ala Pro Gly Gln Gly Leu Glu Trp Ile
            35                  40                  45

Gly Ala Thr Asn Pro Asn Asn Gly Tyr Thr Asp Tyr Asn Gln Arg Phe
        50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser
        115
```

<210> SEQ ID NO 62
<211> LENGTH: 115
<212> TYPE: PRT
<213> ORGANISM: Artificial Sequence
<220> FEATURE:
<223> OTHER INFORMATION: Synthesized

<400> SEQUENCE: 62

```
Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
                20                  25                  30

Trp Met Asn Trp Val Arg Gln Ala Pro Gly Gln Gly Leu Glu Trp Ile
            35                  40                  45

Gly Ala Thr Asn Pro Asn Asn Gly Tyr Thr Asp Tyr Asn Gln Arg Phe
        50                  55                  60

Lys Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser
        115
```

<210> SEQ ID NO 63
<211> LENGTH: 402
<212> TYPE: DNA
<213> ORGANISM: Artificial Sequence
<220> FEATURE:
<223> OTHER INFORMATION: Synthesized

<400> SEQUENCE: 63
atggagttcg gcctgtcctg gctgttcctg gtggccatcc tgaagggcgt gcagtgccag      60

| | |
|---|---|
| gtgcagctgg tgcagtccgg cgccgagctg aagaagcccg gctcctccgt gaaggtgtcc | 120 |
| tgcaaggcct ccggctacac cttcaccaac tactggatga actgggtgcg ccaggccccc | 180 |
| ggccagggcc tggagtggat cggcgccacc aaccccaaca cggctacac cgactacaac | 240 |
| cagcgcttca aggaccgcgc caccctgacc gccgacaagt ccaccaacac cgcctacatg | 300 |
| gagctgtcct ccctgcgctc cgaggacacc gccgtgtact actgcgcccg cggcggccac | 360 |
| ctggcctact ggggccaggg caccctggtg accgtgtcct cc | 402 |

<210> SEQ ID NO 64
<211> LENGTH: 402
<212> TYPE: DNA
<213> ORGANISM: Artificial Sequence
<220> FEATURE:
<223> OTHER INFORMATION: Synthesized

<400> SEQUENCE: 64

| | |
|---|---|
| atggagttcg gcctgtcctg gctgttcctg gtggccatcc tgaagggcgt gcagtgccag | 60 |
| gtgcagctgg tgcagtccgg cgccgagctg aagaagcccg gctcctccgt gaaggtgtcc | 120 |
| tgcaaggcct ccggctacac cttcaccaac tactggatga actgggtgcg ccaggccccc | 180 |
| ggccagggcc tggagtggat cggcgccacc aaccccaaca cggctacac cgactacaac | 240 |
| cagcgcttca aggaccgcgt gaccatcacc gccgacaagt ccaccaacac cgcctacatg | 300 |
| gagctgtcct ccctgcgctc cgaggacacc gccgtgtact actgcgcccg cggcggccac | 360 |
| ctggcctact ggggccaggg caccctggtg accgtgtcct cc | 402 |

<210> SEQ ID NO 65
<211> LENGTH: 402
<212> TYPE: DNA
<213> ORGANISM: Artificial Sequence
<220> FEATURE:
<223> OTHER INFORMATION: Synthesized

<400> SEQUENCE: 65

| | |
|---|---|
| atggagttcg gcctgtcctg gctgttcctg gtggccatcc tgaagggcgt gcagtgccag | 60 |
| gtgcagctgg tgcagtccgg cgccgagctg aagaagcccg gctcctccgt gaaggtgtcc | 120 |
| tgcaaggcct ccggctacac cttcaccaac tactggatga actgggtgcg ccaggccccc | 180 |
| ggccagggcc tggagtggat cggcgccacc aaccccaaca cggctacac cgactacaac | 240 |
| cagcgcttca aggaccgcgc caccctgacc gccgacaagt ccaccaacac cgcctacatg | 300 |
| gagctgtcct ccctgcgctc cgaggacacc gccgtgtact tctgcgcctc cggcggccac | 360 |
| ctggcctact ggggccaggg caccctggtg accgtgtcct cc | 402 |

<210> SEQ ID NO 66
<211> LENGTH: 402
<212> TYPE: DNA
<213> ORGANISM: Artificial Sequence
<220> FEATURE:
<223> OTHER INFORMATION: Synthesized

<400> SEQUENCE: 66

| | |
|---|---|
| atggagttcg gcctgtcctg gctgttcctg gtggccatcc tgaagggcgt gcagtgccag | 60 |
| gtgcagctgg tgcagtccgg cgccgagctg aagaagcccg gctcctccgt gaaggtgtcc | 120 |
| tgcaaggcct ccggctacac cttcaccaac tactggatga actgggtgcg ccaggccccc | 180 |
| ggccagggcc tggagtggat cggcgccacc aaccccaaca cggctacac cgactacaac | 240 |
| cagcgcttca aggaccgcgc caccctgacc gccgacaagt ccaccaacac cgcctacatg | 300 |

```
gagctgtcct ccctgcgctc cgaggacacc gccgtgtact actgcgcctc cggcggccac    360
ctggcctact ggggccaggg caccctggtg accgtgtcct cc                       402
```

<210> SEQ ID NO 67
<211> LENGTH: 402
<212> TYPE: DNA
<213> ORGANISM: Artificial Sequence
<220> FEATURE:
<223> OTHER INFORMATION: Synthesized

<400> SEQUENCE: 67

```
atggagttcg gcctgtcctg gctgttcctg gtggccatcc tgaagggcgt gcagtgccag     60
gtgcagctgg tgcagtccgg cgccgagctg aagaagcccg gctcctccgt gaaggtgtcc    120
tgcaaggcct ccggctacac cttcaccaac tactggatga actgggtgcg ccaggccccc    180
ggccagggcc tggagtggat cggcgccacc aaccccaaca acggctacac cgactacaac    240
cagcgcttca aggaccgcgt gaccatcacc gccgacaagt ccaccaacac cgcctacatg    300
gagctgtcct ccctgcgctc cgaggacacc gccgtgtact actgcgccag cggcggccac    360
ctggcctact ggggccaggg caccctggtg accgtgtcct cc                       402
```

<210> SEQ ID NO 68
<211> LENGTH: 112
<212> TYPE: PRT
<213> ORGANISM: Artificial Sequence
<220> FEATURE:
<223> OTHER INFORMATION: Synthesized

<400> SEQUENCE: 68

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
            100                 105                 110
```

<210> SEQ ID NO 69
<211> LENGTH: 112
<212> TYPE: PRT
<213> ORGANISM: Artificial Sequence
<220> FEATURE:
<223> OTHER INFORMATION: Synthesized

<400> SEQUENCE: 69

```
Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45
```

```
Pro Lys Leu Leu Ile Asn Arg Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
             85                  90                  95

Ala His Val Pro Trp Thr Phe Gly Gly Gly Thr Lys Val Glu Ile Lys
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: Synthesized

<400> SEQUENCE: 70

Asp Ile Val Met Thr Gln Ser Pro Leu Ser Leu Ser Val Ser Pro Gly
 1               5                  10                  15

Glu Pro Ala Ser Ile Ser Cys Arg Ser Ser Gln Ser Leu Phe His Ser
             20                  25                  30

Lys Gly Asn Thr Tyr Leu His Trp Tyr Leu Gln Lys Pro Gly Gln Ser
         35                  40                  45

Pro Lys Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
             85                  90                  95

Ala His Val Pro Trp Thr Phe Gly Gly Gly Thr Lys Val Glu Ile Lys
            100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Synthesized

<400> SEQUENCE: 71

Asp Val Val Met Thr Gln Ser Pro Leu Ser Leu Ser Val Ser Pro Gly
 1               5                  10                  15

Glu Pro Ala Ser Ile Ser Cys Arg Ser Ser Gln Ser Leu Phe His Ser
             20                  25                  30

Lys Gly Asn Thr Tyr Leu His Trp Tyr Leu Gln Lys Pro Gly Gln Ser
         35                  40                  45

Pro Gln Leu Leu Ile Asn Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
             85                  90                  95

Ala His Val Pro Trp Thr Phe Gly Gly Gly Thr Lys Val Glu Ile Lys
            100                 105                 110

<210> SEQ ID NO 72
<211> LENGTH: 112
<212> TYPE: PRT
<213> ORGANISM: Artificial Sequence
```

<220> FEATURE:
<223> OTHER INFORMATION: Synthesized

<400> SEQUENCE: 72

Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110

<210> SEQ ID NO 73
<211> LENGTH: 402
<212> TYPE: DNA
<213> ORGANISM: Artificial Sequence
<220> FEATURE:
<223> OTHER INFORMATION: Synthesized

<400> SEQUENCE: 73
atggacatgc gcgtgcccgc ccagctgctg ggcctgctga tgctgtgggt gtccggctcc      60
tccggcgacg tggtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc cccaagctgc tgatcaaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact tctgctccca gtccgcccac     360
gtgccctgga ccttcggcgg cggcaccaag gtggagatca ag                        402

<210> SEQ ID NO 74
<211> LENGTH: 402
<212> TYPE: DNA
<213> ORGANISM: Artificial Sequence
<220> FEATURE:
<223> OTHER INFORMATION: Synthesized

<400> SEQUENCE: 74
atggacatgc gcgtgcccgc ccagctgctg ggcctgctga tgctgtgggt gtccggctcc      60
tccggcgaca tcgtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc cccaagctgc tgatctaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact actgctccca gtccgcccac     360
gtgccctgga ccttcggcgg cggcaccaag gtggagatca ag                        402

<210> SEQ ID NO 75
<211> LENGTH: 402
<212> TYPE: DNA
<213> ORGANISM: Artificial Sequence
<220> FEATURE:
<223> OTHER INFORMATION: Synthesized

<400> SEQUENCE: 75

```
atggacatgc gcgtgcccgc ccagctgctg ggcctgctga tgctgtgggt gtccggctcc    60
tccggcgacg tggtgatgac ccagtccccc ctgtccctgt ccgtgtcccc cggcgagccc   120
gcctccatct cctgccgctc ctcccagtcc ctgttccact ccaagggcaa cacctacctg   180
cactggtacc tgcagaagcc cggccagtcc ccccagctgc tgatcaaccg cgtgtccaac   240
cgcttctccg gcgtgcccga ccgcttctcc ggctccggct ccggcaccga cttcaccctg   300
aagatctccc gcgtggaggc cgaggacgtg ggcgtgtact tctgctccca gtccgcccac   360
gtgccctgga ccttcggcgg cggcaccaag gtggagatca ag                      402
```

<210> SEQ ID NO 76
<211> LENGTH: 402
<212> TYPE: DNA
<213> ORGANISM: Artificial Sequence
<220> FEATURE:
<223> OTHER INFORMATION: Synthesized

<400> SEQUENCE: 76

```
atggacatgc gcgtgcccgc ccagctgctg ggcctgctga tgctgtgggt gtccggctcc    60
tccggcgaca tcgtgatgac ccagtccccc ctgtccctgt ccgtgtcccc cggcgagccc   120
gcctccatct cctgccgctc ctcccagtcc ctgttccact ccaagggcaa cacctacctg   180
cactggtacc tgcagaagcc cggccagtcc ccccagctgc tgatctaccg cgtgtccaac   240
cgcttctccg gcgtgcccga ccgcttctcc ggctccggct ccggcaccga cttcaccctg   300
aagatctccc gcgtggaggc cgaggacgtg ggcgtgtact actgctccca gtccgcccac   360
gtgccctgga ccttcggcgg cggcaccaag gtggagatca ag                      402
```

<210> SEQ ID NO 77
<211> LENGTH: 321
<212> TYPE: DNA
<213> ORGANISM: Artificial Sequence
<220> FEATURE:
<223> OTHER INFORMATION: Synthesized

<400> SEQUENCE: 77

```
actgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat caggggctga gctcgcccgt cacaaagagc   300
ttcaacaggg gagagtgtta g                                             321
```

<210> SEQ ID NO 78
<211> LENGTH: 35
<212> TYPE: PRT
<213> ORGANISM: Artificial Sequence
<220> FEATURE:
<223> OTHER INFORMATION: Synthesized

<400> SEQUENCE: 78

```
Glu Gln Val Thr Asn Val Gly Gly Ala Val Val Thr Gly Val Thr Ala
1               5                   10                  15

Val Ala Gln Lys Thr Val Glu Gly Ala Gly Ser Ile Ala Ala Ala Thr
```

```
              20                  25                  30

Gly Phe Val
        35

<210> SEQ ID NO 79
<211> LENGTH: 28
<212> TYPE: PRT
<213> ORGANISM: Artificial Sequence
<220> FEATURE:
<223> OTHER INFORMATION: Synthesized

<400> SEQUENCE: 79

Lys Glu Gln Val Thr Asn Val Gly Gly Ala Val Val Thr Gly Val Thr
1               5                   10                  15

Ala Val Ala Gln Lys Thr Val Glu Gly Ala Gly Ser
            20                  25

<210> SEQ ID NO 80
<211> LENGTH: 405
<212> TYPE: DNA
<213> ORGANISM: Artificial Sequence
<220> FEATURE:
<223> OTHER INFORMATION: Synthesized

<400> SEQUENCE: 80
atgggatgga gctgggtctt tatcttcctc ctgtcaggaa ctgcaggtgt ccattgccag      60
gtccagctgc agcagtctgg acctgagctg gtgaagcctg ggacttcagt gaagatatcc    120
tgcaaggctt ctggctacag cttcacaagc tactatatac actgggtgaa gcagagtcct    180
ggacagggac ttgagtggat tggatggatt tatcctggaa gtggtaatac taagtacagt    240
gagaagttca aggcaaggc cacactgact gcagacacat cctccagcac agcctacatg     300
cagctcagca gcctgacatc tgaggactct gcagtctatt tctgtgcaag agatggttgc    360
tacgggtttg cttactgggg ccaagggact ctggtcactg tctct                    405

<210> SEQ ID NO 81
<211> LENGTH: 135
<212> TYPE: PRT
<213> ORGANISM: Artificial Sequence
<220> FEATURE:
<223> OTHER INFORMATION: Synthesized

<400> SEQUENCE: 81

Met Gly Trp Ser Trp Val Phe Ile Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Thr Ser Val Lys Ile Ser Cys Lys Ala Ser Gly Tyr Ser Phe
        35                  40                  45

Thr Ser Tyr Tyr Ile His Trp Val Lys Gln Ser Pro Gly Gln Gly Leu
    50                  55                  60

Glu Trp Ile Gly Trp Ile Tyr Pro Gly Ser Gly Asn Thr Lys Tyr Ser
65                  70                  75                  80

Glu Lys Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Asp Gly Cys Tyr Gly Phe Ala Tyr Trp Gly Gln
        115                 120                 125
```

```
<210> SEQ ID NO 82
<211> LENGTH: 393
<212> TYPE: DNA
<213> ORGANISM: Artificial Sequence
<220> FEATURE:
<223> OTHER INFORMATION: Synthesized

<400> SEQUENCE: 82
atggagacag acacactcct gttatgggtg ctgctgctct gggttccagg ctccactggt      60
gacattgtgc tgacccaatc tccagcttct ttggctgtgt ctctagggca gagggccacc     120
atctcctgca aggccagcca aagtgttgat tatgatggtg atagttatat gaactggtac     180
caacagaaac caggacagcc acccaaattc ctcatctgtg ctgcatccaa tctagaatct     240
gggatcccag ccaggtttag tggcagtggg tctgggacag acttcaccct caacatccat     300
cctgtggagg aggaggatgc tgcaacctat tactgtcagc aaagtaatga ggatccattc     360
acgttcggct cggggacaaa gttggaaata aaa                                  393

<210> SEQ ID NO 83
<211> LENGTH: 131
<212> TYPE: PRT
<213> ORGANISM: Artificial Sequence
<220> FEATURE:
<223> OTHER INFORMATION: Synthesized

<400> SEQUENCE: 83

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Phe Leu Ile Cys Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Phe Thr Phe Gly Ser Gly Thr Lys Leu
        115                 120                 125

Glu Ile Lys
    130

<210> SEQ ID NO 84
<211> LENGTH: 345
<212> TYPE: DNA
<213> ORGANISM: Artificial Sequence
<220> FEATURE:
<223> OTHER INFORMATION: Synthesized

<400> SEQUENCE: 84
gtccagctgc agcagtctgg acctgagctg gtgaagcctg gacttcagt gaagatatcc       60
tgcaaggctt ctggctacag cttcacaagc tactatatac actgggtgaa gcagagtcct     120
ggacagggac ttgagtggat tggatggatt tatcctggaa gtggtaatac taagtacagt     180
```

```
gagaagttca agggcaaggc cacactgact gcagacacat cctccagcac agcctacatg    240
cagctcagca gcctgacatc tgaggactct gcagtctatt tctgtgcaag agatggttgc    300
tacgggtttg cttactgggg ccaagggact ctggtcactg tctct                   345
```

<210> SEQ ID NO 85
<211> LENGTH: 115
<212> TYPE: PRT
<213> ORGANISM: Artificial Sequence
<220> FEATURE:
<223> OTHER INFORMATION: Synthesized

<400> SEQUENCE: 85

```
Val Gln Leu Gln Gln Ser Gly Pro Glu Leu Val Lys Pro Gly Thr Ser
1               5                   10                  15

Val Lys Ile Ser Cys Lys Ala Ser Gly Tyr Ser Phe Thr Ser Tyr Tyr
            20                  25                  30

Ile His Trp Val Lys Gln Ser Pro Gly Gln Gly Leu Glu Trp Ile Gly
        35                  40                  45

Trp Ile Tyr Pro Gly Ser Gly Asn Thr Lys Tyr Ser Glu Lys Phe Lys
    50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Asp Gly Cys Tyr Gly Phe Ala Tyr Trp Gly Gln Gly Thr Leu Val
            100                 105                 110

Thr Val Ser
        115
```

<210> SEQ ID NO 86
<211> LENGTH: 333
<212> TYPE: DNA
<213> ORGANISM: Artificial Sequence
<220> FEATURE:
<223> OTHER INFORMATION: Synthesized

<400> SEQUENCE: 86

```
gacattgtgc tgacccaatc tccagcttct ttggctgtgt ctctagggca gagggccacc    60
atctcctgca aggccagcca aagtgttgat tatgatggtg atagttatat gaactggtac   120
caacagaaac caggacagcc acccaaattc ctcatctgtg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtaatga ggatccattc   300
acgttcggct cggggacaaa gttggaaata aaa                                333
```

<210> SEQ ID NO 87
<211> LENGTH: 111
<212> TYPE: PRT
<213> ORGANISM: Artificial Sequence
<220> FEATURE:
<223> OTHER INFORMATION: Synthesized

<400> SEQUENCE: 87

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30
```

Gly Asp Ser Tyr Met Asn Trp Tyr Gln Gln Lys Pro Gly Gln Pro Pro
          35                  40                  45

Lys Phe Leu Ile Cys Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
              85                  90                  95

Glu Asp Pro Phe Thr Phe Gly Ser Gly Thr Lys Leu Glu Ile Lys
            100                 105                 110

<210> SEQ ID NO 88
<211> LENGTH: 5
<212> TYPE: PRT
<213> ORGANISM: Artificial Sequence
<220> FEATURE:
<223> OTHER INFORMATION: Synthesized

<400> SEQUENCE: 88

Ser Tyr Tyr Ile His
1               5

<210> SEQ ID NO 89
<211> LENGTH: 17
<212> TYPE: PRT
<213> ORGANISM: Artificial Sequence
<220> FEATURE:
<223> OTHER INFORMATION: Synthesized

<400> SEQUENCE: 89

Trp Ile Tyr Pro Gly Ser Gly Asn Thr Lys Tyr Ser Glu Lys Phe Lys
1               5                   10                  15

Gly

<210> SEQ ID NO 90
<211> LENGTH: 8
<212> TYPE: PRT
<213> ORGANISM: Artificial Sequence
<220> FEATURE:
<223> OTHER INFORMATION: Synthesized

<400> SEQUENCE: 90

Asp Gly Cys Tyr Gly Phe Ala Tyr
1               5

<210> SEQ ID NO 91
<211> LENGTH: 15
<212> TYPE: PRT
<213> ORGANISM: Artificial Sequence
<220> FEATURE:
<223> OTHER INFORMATION: Synthesized

<400> SEQUENCE: 91

Lys Ala Ser Gln Ser Val Asp Tyr Asp Gly Asp Ser Tyr Met Asn
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: Synthesized

<400> SEQUENCE: 92

Ala Ala Ser Asn Leu Glu Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Synthesized

<400> SEQUENCE: 93

Gln Gln Ser Asn Glu Asp Pro Phe Thr
1               5

<210> SEQ ID NO 94
<211> LENGTH: 351
<212> TYPE: DNA
<213> ORGANISM: Artificial Sequence
<220> FEATURE:
<223> OTHER INFORMATION: Synthesized

<400> SEQUENCE: 94
caggtgcagc tggtgcagtc cggcgccgag ctgaagaagc ccggcgcctc cgtgaaggtg        60
tcctgcaagg cctccggcta ctccttcacc tcctactaca tccactgggt gaagcaggcc       120
cccggccagg gcctggagtg gatcggctgg atctaccccg gctccggcaa caccaagtac       180
tccgagaagt tcaagggccg cgccaccctg accgccgaca cctccacctc caccgcctac       240
atggagctgc gctccctgcg ctccgacgac accgccgtgt acttctgcgc ccgcgacggc       300
tgctacggct cgcctactg gggccagggc accctggtga ccgtgtcctc a                 351

<210> SEQ ID NO 95
<211> LENGTH: 117
<212> TYPE: PRT
<213> ORGANISM: Artificial Sequence
<220> FEATURE:
<223> OTHER INFORMATION: Synthesized

<400> SEQUENCE: 95

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Ser Phe Thr Ser Tyr
                20                  25                  30

Tyr Ile His Trp Val Lys Gln Ala Pro Gly Gln Gly Leu Glu Trp Ile
            35                  40                  45

Gly Trp Ile Tyr Pro Gly Ser Gly Asn Thr Lys Tyr Ser Glu Lys Phe
        50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Cys Tyr Gly Ser Pro Tyr Trp Gly Gln Gly Thr Leu
            100                 105                 110

Val Thr Val Ser Ser
        115

<210> SEQ ID NO 96
<211> LENGTH: 351
<212> TYPE: DNA
<213> ORGANISM: Artificial Sequence
<220> FEATURE:
<223> OTHER INFORMATION: Synthesized

<400> SEQUENCE: 96

```
caggtgcagc tggtgcagtc cggcgccgag gtgaagaagc ccggcgcctc cgtgaaggtg      60
tcctgcaagg cctccggcta ctccttcacc tcctactaca tccactgggt gcgccaggcc     120
cccggccagg gcctggagtg gatcggctgg atctacccg gctccggcaa caccaagtac      180
tccgagaagt tcaagggccg cgccaccctg accgccgaca cctccacctc caccgcctac     240
atggagctgc gctccctgcg ctccgacgac accgccgtgt acttctgcgc ccgcgacggc     300
tgctacggct cgcctactg gggccagggc accctggtga ccgtgtcctc a               351
```

<210> SEQ ID NO 97
<211> LENGTH: 117
<212> TYPE: PRT
<213> ORGANISM: Artificial Sequence
<220> FEATURE:
<223> OTHER INFORMATION: Synthesized

<400> SEQUENCE: 97

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Cys Tyr Gly Phe Ala Tyr Trp Gly Gln Gly Thr Leu
            100                 105                 110

Val Thr Val Ser Ser
        115
```

<210> SEQ ID NO 98
<211> LENGTH: 351
<212> TYPE: DNA
<213> ORGANISM: Artificial Sequence
<220> FEATURE:
<223> OTHER INFORMATION: Synthesized

<400> SEQUENCE: 98

```
caggtgcagc tggtgcagtc cggcgccgag gtgaagaagc ccggcgcctc cgtgaaggtg      60
tcctgcaagg cctccggcta caccttcacc tcctactaca tccactgggt gcgccaggcc     120
cccggccagg gcctggagtg gatgggctgg atctaccccg gctccggcaa caccaagtac     180
tccgagaagt tcaagggccg cgccaccatg accgccgaca cctccacctc caccgcctac     240
atggagctgc gctccctgcg ctccgacgac accgccgtgt actactgcgc ccgcgacggc     300
tgctacggct cgcctactg gggccagggc accctggtga ccgtgtcctc a               351
```

<210> SEQ ID NO 99
<211> LENGTH: 117
<212> TYPE: PRT
<213> ORGANISM: Artificial Sequence
<220> FEATURE:
<223> OTHER INFORMATION: Synthesized

<400> SEQUENCE: 99

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser
        115
```

<210> SEQ ID NO 100
<211> LENGTH: 351
<212> TYPE: DNA
<213> ORGANISM: Artificial Sequence
<220> FEATURE:
<223> OTHER INFORMATION: Synthesized

<400> SEQUENCE: 100

```
caggtgcagc tggtgcagtc cggcgccgag gtgaagaagc ccggcgcctc cgtgaaggtg      60
tcctgcaagg cctccggcta ctccttcacc tcctactaca tccactgggt cgccaggcc     120
cccggccagg gcctggagtg gatcggctgg atctaccccg gctccggcaa caccaagtac    180
tccgagaagt tcaagggccg cgccaccctg accgccgaca cctccacctc caccgcctac    240
atggagctgc gctccctgcg ctccgacgac accgccgtgt acttctgcgc ccgcgacggc    300
tcctacggct cgcctactg gggccagggc accctggtga ccgtgtcctc a              351
```

<210> SEQ ID NO 101
<211> LENGTH: 117
<212> TYPE: PRT
<213> ORGANISM: Artificial Sequence
<220> FEATURE:
<223> OTHER INFORMATION: Synthesized

<400> SEQUENCE: 101

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Ser Tyr Gly Phe Ala Tyr Trp Gly Gln Gly Thr Leu
            100                 105                 110
```

Val Thr Val Ser Ser
        115

<210> SEQ ID NO 102
<211> LENGTH: 351
<212> TYPE: DNA
<213> ORGANISM: Artificial Sequence
<220> FEATURE:
<223> OTHER INFORMATION: Synthesized

<400> SEQUENCE: 102
caggtgcagc tggtgcagtc cggcgccgag gtgaagaagc ccggcgcctc cgtgaaggtg      60
tcctgcaagg cctccggcta caccttcacc tcctactaca tccactgggt gcgccaggcc     120
cccggccagg gcctggagtg gatgggctgg atctaccccg gctccggcaa caccaagtac     180
tccgagaagt tcaagggccg cgccaccatg accgccgaca cctccacctc caccgcctac     240
atggagctgc gctccctgcg ctccgacgac accgccgtgt actactgcgc ccgcgacggc     300
tcctacggct cgcctactg gggccagggc accctggtga ccgtgtcctc a               351

<210> SEQ ID NO 103
<211> LENGTH: 117
<212> TYPE: PRT
<213> ORGANISM: Artificial Sequence
<220> FEATURE:
<223> OTHER INFORMATION: Synthesized

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Ser Tyr Gly Phe Ala Tyr Trp Gly Gln Gly Thr Leu
            100                 105                 110

Val Thr Val Ser Ser
        115

<210> SEQ ID NO 104
<211> LENGTH: 57
<212> TYPE: DNA
<213> ORGANISM: Artificial Sequence
<220> FEATURE:
<223> OTHER INFORMATION: Synthesized

<400> SEQUENCE: 104
atggagttcg gcctgtcctg gctgttcctg gtggccatcc tgaagggcgt gcagtgc          57

<210> SEQ ID NO 105
<211> LENGTH: 19
<212> TYPE: PRT
<213> ORGANISM: Artificial Sequence
<220> FEATURE:
<223> OTHER INFORMATION: Synthesized -continued

<400> SEQUENCE: 105

Met Glu Phe Gly Leu Ser Trp Leu Phe Leu Val Ala Ile Leu Lys Gly
1               5                   10                  15

Val Gln Cys

<210> SEQ ID NO 106
<211> LENGTH: 57
<212> TYPE: DNA
<213> ORGANISM: Artificial Sequence
<220> FEATURE:
<223> OTHER INFORMATION: Synthesized

<400> SEQUENCE: 106

```
atggactgga cctggagcat cctttcttg gtggcagcag caacaggtgc ccactcc        57
```

<210> SEQ ID NO 107
<211> LENGTH: 19
<212> TYPE: PRT
<213> ORGANISM: Artificial Sequence
<220> FEATURE:
<223> OTHER INFORMATION: Synthesized

<400> SEQUENCE: 107

Met Asp Trp Thr Trp Ser Ile Leu Phe Leu Val Ala Ala Ala Thr Gly
1               5                   10                  15

Ala His Ser

<210> SEQ ID NO 108
<211> LENGTH: 333
<212> TYPE: DNA
<213> ORGANISM: Artificial Sequence
<220> FEATURE:
<223> OTHER INFORMATION: Synthesized

<400> SEQUENCE: 108

```
gacatccagc tgacccagtc cccctcctcc ctgtccgcct ccgtgggcga ccgcgtgacc     60
atcacctgca aggcctccca gtccgtggac tacgacggcg actcctacat gaactggtac    120
cagcagaagc ccggcaaggc ccccaagttc ctgatctgcg ccgcctccaa cctggagtcc    180
ggcgtgccct cccgcttctc cggctccggc tccggcaccg acttcaccct gaccatctcc    240
tccctgcagc ccgaggacgc cgccacctac tactgccagc agtccaacga ggacccctc    300
accttcggcc agggcaccaa gctggagatc aag                                  333
```

<210> SEQ ID NO 109
<211> LENGTH: 111
<212> TYPE: PRT
<213> ORGANISM: Artificial Sequence
<220> FEATURE:
<223> OTHER INFORMATION: Synthesized

<400> SEQUENCE: 109

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Phe Leu Ile Cys Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser

Ser Leu Gln Pro Glu Asp Ala Ala Thr Tyr Tyr Cys Gln Gln Ser Asn
65                  70                  75                  80

Ser Leu Gln Pro Glu Asp Ala Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 110
<211> LENGTH: 333
<212> TYPE: DNA
<213> ORGANISM: Artificial Sequence
<220> FEATURE:
<223> OTHER INFORMATION: Synthesized

<400> SEQUENCE: 110
gacatccagc tgacccagtc cccctcctcc ctgtccgcct ccgtgggcga ccgcgtgacc      60
atcacctgca aggcctccca gtccgtggac tacgacggcg actcctacat gaactggtac     120
cagcagaagc ccggcaaggc ccccaagttc ctgatctacg ccgcctccaa cctggagtcc     180
ggcgtgccct cccgcttctc cggctccggc tccggcaccg acttcaccct gaccatctcc     240
tccctgcagc ccgaggacgc cgccacctac tactgccagc agtccaacga ggacccttc     300 accttcggcc agggcaccaa gctggagatc aag                                  333

<210> SEQ ID NO 111
<211> LENGTH: 111
<212> TYPE: PRT
<213> ORGANISM: Artificial Sequence
<220> FEATURE:
<223> OTHER INFORMATION: Synthesized

<400> SEQUENCE: 111

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Phe Leu Ile Tyr Ala Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 112
<211> LENGTH: 333
<212> TYPE: DNA
<213> ORGANISM: Artificial Sequence
<220> FEATURE:
<223> OTHER INFORMATION: Synthesized

<400> SEQUENCE: 112
gacatccagc tgacccagtc cccctcctcc ctgtccgcct ccgtgggcga ccgcgtgacc      60
atcacctgca aggcctccca gtccgtggac tacgacggcg actcctacat gaactggtac     120
cagcagaagc ccggcaaggc ccccaagttc ctgatctgcg ccgcctccaa cctggagtcc     180
ggcgtgccct cccgcttctc cggctccggc tccggcaccg acttcaccct gaccatctcc     240

```
tccctgcagc ccgaggactt cgccacctac tactgccagc agtccaacga ggaccccttc      300
accttcggcc agggcaccaa gctggagatc aag                                   333
```

<210> SEQ ID NO 113
<211> LENGTH: 111
<212> TYPE: PRT
<213> ORGANISM: Artificial Sequence
<220> FEATURE:
<223> OTHER INFORMATION: Synthesized

<400> SEQUENCE: 113

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 114
<211> LENGTH: 333
<212> TYPE: DNA
<213> ORGANISM: Artificial Sequence
<220> FEATURE:
<223> OTHER INFORMATION: Synthesized

<400> SEQUENCE: 114

```
gacatccagc tgacccagtc cccctcctcc ctgtccgcct ccgtgggcga ccgcgtgacc       60
atcacctgca aggcctccca gtccgtggac tacgacggcg actcctacat gaactggtac      120
cagcagaagc ccggcaaggc ccccaagttc ctgatctacg ccgcctccaa cctggagtcc      180
ggcgtgccct cccgcttctc cggctccggc tccggcaccg acttcaccct gaccatctcc      240
tccctgcagc ccgaggactt cgccacctac tactgccagc agtccaacga ggaccccttc      300
accttcggcc agggcaccaa gctggagatc aag                                   333
```

<210> SEQ ID NO 115
<211> LENGTH: 111
<212> TYPE: PRT
<213> ORGANISM: Artificial Sequence
<220> FEATURE:
<223> OTHER INFORMATION: Synthesized

<400> SEQUENCE: 115

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 116
<211> LENGTH: 66
<212> TYPE: DNA
<213> ORGANISM: Artificial Sequence
<220> FEATURE:
<223> OTHER INFORMATION: Synthesized

<400> SEQUENCE: 116
atggacatgc gcgtgcccgc ccagctgctg ggcctgctga tgctgtgggt gtccggctcc    60
tccggc                                                               66

<210> SEQ ID NO 117
<211> LENGTH: 117
<212> TYPE: PRT
<213> ORGANISM: Artificial Sequence
<220> FEATURE:
<223> OTHER INFORMATION: Synthesized

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Gly Ile Ser Trp Val Arg Gln Ala Pro Gly Gln Gly Leu Glu Trp Met
            35                  40                  45

Gly Trp Ile Ser Pro Tyr Asn Gly Asp Thr Asn Tyr Ala Gln Asn Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Ser Met Ser Asp Tyr Trp Gly Gln Gly Thr Leu
            100                 105                 110

Val Thr Val Ser Ser
        115

<210> SEQ ID NO 118
<211> LENGTH: 107
<212> TYPE: PRT
<213> ORGANISM: Artificial Sequence
<220> FEATURE:
<223> OTHER INFORMATION: Synthesized

<400> SEQUENCE: 118

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Pro
                 85                  90                  95

Thr Phe Gly Gln Gly Thr Lys Leu Glu Ile Lys
                100                 105
```

<210> SEQ ID NO 119
<211> LENGTH: 117
<212> TYPE: PRT
<213> ORGANISM: Artificial Sequence
<220> FEATURE:
<223> OTHER INFORMATION: Synthesized

<400> SEQUENCE: 119

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Tyr
                20                  25                  30

Tyr Ile His Trp Val Arg Gln Ala Pro Gly Gln Gly Leu Glu Trp Met
             35                  40                  45

Gly Trp Ile Tyr Pro Gly Ser Gly Asn Thr Lys Tyr Ser Glu Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asp Gly Cys Tyr Gly Phe Ala Tyr Trp Gly Gln Gly Thr Leu
                100                 105                 110

Val Thr Val Ser Ser
            115
```

<210> SEQ ID NO 120
<211> LENGTH: 111
<212> TYPE: PRT
<213> ORGANISM: Artificial Sequence
<220> FEATURE:
<223> OTHER INFORMATION: Synthesized

<400> SEQUENCE: 120

```
Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
             35                  40                  45

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Phe Thr Phe Gly Gly Gly Thr Lys Leu Glu Ile Lys
                100                 105                 110
```

<210> SEQ ID NO 121
<211> LENGTH: 117
<212> TYPE: PRT
<213> ORGANISM: Artificial Sequence

```
<220> FEATURE:
<223> OTHER INFORMATION: Synthesized
<220> FEATURE:
<221> NAME/KEY: VARIANT
<222> LOCATION: 11
<223> OTHER INFORMATION: Xaa = V or L
<220> FEATURE:
<221> NAME/KEY: VARIANT
<222> LOCATION: 28
<223> OTHER INFORMATION: Xaa = S or T
<220> FEATURE:
<221> NAME/KEY: VARIANT
<222> LOCATION: 38
<223> OTHER INFORMATION: Xaa = R or K
<220> FEATURE:
<221> NAME/KEY: VARIANT
<222> LOCATION: 48
<223> OTHER INFORMATION: Xaa = M or I
<220> FEATURE:
<221> NAME/KEY: VARIANT
<222> LOCATION: 68
<223> OTHER INFORMATION: Xaa = V or A
<220> FEATURE:
<221> NAME/KEY: VARIANT
<222> LOCATION: 70
<223> OTHER INFORMATION: Xaa = M or L
<220> FEATURE:
<221> NAME/KEY: VARIANT
<222> LOCATION: 72
<223> OTHER INFORMATION: Xaa = T or A
<220> FEATURE:
<221> NAME/KEY: VARIANT
<222> LOCATION: 95
<223> OTHER INFORMATION: Xaa = Y or F
<220> FEATURE:
<221> NAME/KEY: VARIANT
<222> LOCATION: 101
<223> OTHER INFORMATION: Xaa = C or S

<400> SEQUENCE: 121

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Xaa Phe Thr Ser Tyr
            20                  25                  30

Tyr Ile His Trp Val Xaa Gln Ala Pro Gly Gln Gly Leu Glu Trp Xaa
        35                  40                  45

Gly Trp Ile Tyr Pro Gly Ser Gly Asn Thr Lys Tyr Ser Glu Lys Phe
    50                  55                  60

Lys Gly Arg Xaa Thr Xaa Thr Xaa Asp Thr Ser Thr Ser Thr Ala Tyr
65                  70                  75                  80

Met Glu Leu Arg Ser Leu Arg Ser Asp Asp Thr Ala Val Tyr Xaa Cys
                85                  90                  95

Ala Arg Asp Gly Xaa Tyr Gly Phe Ala Tyr Trp Gly Gln Gly Thr Leu
            100                 105                 110

Val Thr Val Ser Ser
        115

<210> SEQ ID NO 122
<211> LENGTH: 111
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 50
<223> OTHER INFORMATION: Xaa = L or F
<220> FEATURE:
<221> NAME/KEY: VARIANT
<222> LOCATION: 53
```

```
<223> OTHER INFORMATION: Xaa = Y or C
<220> FEATURE:
<221> NAME/KEY: VARIANT
<222> LOCATION: 87
<223> OTHER INFORMATION: Xaa = F or A

<400> SEQUENCE: 122

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Xaa Leu Ile Xaa Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Xaa Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 123
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 3
<223> OTHER INFORMATION: Xaa = C or M or S or T

<400> SEQUENCE: 123

Asp Gly Xaa Tyr Gly Phe Ala Tyr
1               5

<210> SEQ ID NO 124
<211> LENGTH: 218
<212> TYPE: PRT
<213> ORGANISM: Artificial Sequence
<220> FEATURE:
<223> OTHER INFORMATION: Synthesized

<400> SEQUENCE: 124

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

<210> SEQ ID NO 125
<211> LENGTH: 217
<212> TYPE: PRT
<213> ORGANISM: Artificial Sequence
<220> FEATURE:
<223> OTHER INFORMATION: Synthesized

<400> SEQUENCE: 125

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Phe Leu Ile Cys Ala Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 126
<211> LENGTH: 447
<212> TYPE: PRT
<213> ORGANISM: Artificial Sequence
<220> FEATURE:
<223> OTHER INFORMATION: Synthesized

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Val Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

```
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 127
<211> LENGTH: 447
<212> TYPE: PRT
<213> ORGANISM: Artificial Sequence
<220> FEATURE:
<223> OTHER INFORMATION: Synthesized

<400> SEQUENCE: 127

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Ile His Trp Val Arg Gln Ala Pro Gly Gln Gly Leu Glu Trp Met
            35                  40                  45
Gly Trp Ile Tyr Pro Gly Ser Gly Asn Thr Lys Tyr Ser Glu Lys Phe
    50                  55                  60
Lys Gly Arg Ala Thr Met Thr Ala Asp Thr Ser Ser Thr Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Gly Cys Tyr Gly Phe Ala Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
        210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 128
<211> LENGTH: 326
<212> TYPE: PRT
<213> ORGANISM: Artificial Sequence
<220> FEATURE:
<223> OTHER INFORMATION: Synthesized

<400> SEQUENCE: 128

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 129
<211> LENGTH: 330
<212> TYPE: PRT
<213> ORGANISM: Artificial Sequence
<220> FEATURE:
<223> OTHER INFORMATION: Synthesized

<400> SEQUENCE: 129

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330
```

MONITORING IMMUNOTHERAPY OF LEWY BODY DISEASE FROM CONSTIPATION SYMPTOMS

CROSS REFERENCE TO RELATED APPLICATIONS

The present application is a National Stage Entry of PCT/IB2014/066141 filed Nov. 19, 2014, which claims the benefit of U.S. Provisional Application No. 61/906,372 filed Nov. 19, 2013, each incorporated by reference in it's entirety.

REFERENCE TO A SEQUENCE LISTING

This application includes an electronic sequence listing in a file named 477900_SEQLST.txt, created on May 18, 2016 and containing 119,108 bytes, which is hereby incorporated by reference in its entirety.

BACKGROUND

Lewy body diseases (LBDs) are characterized by degeneration of the dopaminergic system, motor alterations, cognitive impairment, and formation of Lewy bodies (LBs) and/or Lewy neurites. (McKeith et al., Neurology (1996) 47:1113-24). Lewy Body disease include Parkinson's disease (including idiopathic Parkinson's disease), and Lewy Body dementia (LBD). Lewy body diseases are a common cause for movement disorders and cognitive deterioration in the aging population (Galasko et al., Arch. Neurol. (1994) 51:888-95). Constipation is another common symptom of subjects with Lewy body disease (Ondo et al., Neurology 2012; 78; 1650-1654; Ashraf et al., Movement Disorders 12, 946-951 (1997)).

Alpha-synuclein is normally associated with synapses and is believed to play a role in neural plasticity, learning and memory. Alpha-synuclein is also implicated with a central role in pathogenesis of Lewy body disease. The protein can aggregate to form insoluble fibrils in pathological conditions. For example, alpha-synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the alpha-synuclein gene co-segregate with rare familial forms of parkinsonism (Kruger et al., Nature Gen. (1998) 18:106-8; Polvmeropoulos, et al., Science (1997) 276:2045-7). Over expression of alpha-synuclein in transgenic mice (Masliah et al., Science (2000) 287:1265-9) and *Drosophila* (Feany et al., Nature (2000) 404:394-8) mimics several pathological aspects of Lewy body disease. Soluble oligomers of synuclein may be neurotoxic (Conway et al., Proc Natl Acad Sci USA (2000) 97:571-576. The accumulation of alpha-synuclein with similar morphological and neurological alterations in species and animal models as diverse as humans, mice, and flies suggests that this molecule contributes to the development of Lewy body disease.

Immunotherapy directed against alpha-synuclein has been reported to reduce alpha-synuclein deposits and behavioral symptoms in mouse models of Lewy body disease (Masliah et al., PLoS ONE 6(4): e19338. doi:10.1371/journal.pone.0019338). However, effects of immunotherapy on alpha-synuclein deposits are not easy to monitor in human subjects. Effects of immunotherapy on cognitive and motor systems may be slow to develop, and may also be subject to significant day-to-day variation independent of treatment effects.

SUMMARY OF THE CLAIMED INVENTION

The invention provides a method of assessing the efficacy of immunotherapy against alpha-synuclein in subjects diagnosed with a Lewy Body disease and having one or more constipation symptoms, comprising: (a) evaluating the subjects' constipation symptoms before administration of an immunotherapeutic agent in a first regime; (b) administering the immunotherapeutic agent to the subjects in the first regime; (c) evaluating the subjects' constipation symptoms after administering the iummunotherapeutic agent in the first regime, (d) comparing the subjects' constipation symptoms before and after administering the immunotherapeutic agent in the first regime; (e) administering a second regime to subjects whose symptoms improve and a third regime to subjects whose symptoms deteriorate, the second and third regimes being different. Optionally, the second regime is the same as the first regime. Optionally, the second regime administers the same immunotherapy agent as the first regime at a reduced dosage or frequency. Optionally, the third regime administers the same immunotherapy agent as the first regime at an increased dosage or frequency. Optionally, the third regime administers a different immunotherapy agent than the first regime, or a non-immunotherapy agent. Optionally, the Lewy body disease is Parkinson's disease or dementia with Lewy bodies.

In any of the above methods, the immunotherapy agent can be an antibody that specifically binds to alpha-synuclein. Optionally, the immunotherapy agent induces an antibody that specifically binds to alpha-synuclein. Optionally, the antibody binds to an epitope within residues 1-10, 91-99, 118-126 or 130-140 of alpha-synuclein. Optionally, the antibody binds to an epitope within residues 118-126 of alpha-synuclein. Optionally, the antibody comprising the six Kabat CDRs of 9E4, 5C1, 1H7, 6H7, or 8A5. Optionally, the antibody is humanized 9E4 comprising a heavy chain variable region of SEQ ID NO:37 and a light chain variable region of SEQ ID NO:32.

In any of the above methods, the subject's one or more constipation symptoms can evaluated from subject answers to a questionnaire. Optionally, the questionnaire is the PAC-SYM questionnaire. Optionally, the subjects' constipation symptoms are evaluated on at least first and second occasions respectively after first and second administrations of the immunotherapy agent in the first regime. Optionally the dose or frequency is reduced by at least half in the second regime relative to the first regime. Optionally, the dose or frequency is increased by at least a factor of two in the third regime relative to the second regime.

Any of the above methods can further comprise monitoring the subjects for changes in one or more signs or symptoms of the Lewy body disease other than constipation in response to the first regime. Optionally, the signs or symptoms include motor functioning, cognitive function, and level of alpha-synuclein in the brain or body fluid.

The invention further provides a method of treating constipation in a subject with a Lewy body disease and having one or more symptoms of constipation. The method comprises administering immunotherapy against alpha-synuclein to the subject in a regime effective to reduce the constipation symptoms. Optionally, the method includes monitoring the constipation symptoms.

The invention further provides a method of evaluating an immunotherapy regime. Such a method comprises administering an immunotherapy regime against alpha-synuclein to a transgenic animal model expressing an alpha-synuclein transgene and disposed to develop signs and symptoms of a Lewy body disease; and determining one or more symptoms of constipation before and after administering the immunotherapy regime, and improvement of the symptoms providing an indication that the immunotherapy regime is useful for treating Lewy body disease.

The invention further provides a method of assessing the efficacy of immunotherapy against alpha-synuclein in a subject diagnosed with a Lewy Body disease and having one or more constipation symptoms, comprising: (a) evaluating the subject's constipation symptoms before administration of an immunotherapeutic agent in a first regime; (b) administering the immunotherapeutic agent to the subject in the first regime; (c) evaluating the subject's constipation symptoms after administering the immunotherapeutic agent in the first regime, (d) comparing the subject's constipation symptoms before and after administering the immunotherapeutic agent in the first regime; wherein the subject's symptoms improve; and (e) administering a second regime, which is the same as the first regime, or which administering the same immunotherapeutic agent as the first regime at a reduced dose or frequency.

The invention further provides a method of assessing the efficacy of immunotherapy against alpha-synuclein in a subject diagnosed with a Lewy Body disease and having one or more constipation symptoms, comprising: (a) evaluating the subject's constipation symptoms before administration of an immunotherapeutic agent in a first regime; (b) administering the immunotherapeutic agent to the subject in the first regime; (c) evaluating the subject's constipation symptoms after administering the immunotherapeutic agent in the first regime, (d) comparing the subject's constipation symptoms before and after administering the immunotherapeutic agent in the first regime; wherein the subject's symptoms remain the same or deteriorate; and (e) administering a second regime, which administers the same immunotherapeutic agent as the first regime at an increased dose or frequency or which administers a different immunotherapeutic agent or which administers a non-immunotherapeutic agent effective for treatment of Lewy body disease.

In any of the above methods, the immunotherapeutic agent can be a humanized 9E4 antibody and the dose can be 0.3 mg/kg, 1.0-3.0 mg/kg, 3.0-10 mg/kg or 10-30 mg/kg administered with a frequency of once every 28-31 days, optionally monthly.

The invention further provides a method of treating or effecting prophylaxis of a subject with a Lewy body disease, comprising administering a humanized 9E4 antibody to the subject at a dose of 0.3 mg/kg to 30 mg/kg at a frequency of once every 28-31 days, optionally monthly. Optionally, the dose is 0.3-1.0 mg/kg. Optionally, the dose is 1.0-3.0 mg/kg. Optionally, the dose is 3.0-10 mg/kg. Optionally, the dose is 10-30 mg/kg. Optionally, the dose is 0.3 mg/kg. Optionally, the dose is 1.0 mg/kg. Optionally, the dose is 3 mg/kg. Optionally, the dose is 10 mg/kg. Optionally, the dose is 30 mg/kg. In any of these methods the humanized 9E4 antibody can have a light chain variable region of SEQ ID NO:32 and a heavy chain variable region of SEQ ID NO:37.

Definitions

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The basic antibody structural unit is a tetramer of subunits. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally. *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions (with gaps not counted) multiplied by 100 to convert to percentage.

For purposes of classifying amino acids substitutions as conservative or non-conservative, amino acids are grouped as follows: Group I (hydrophobic sidechains): Norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys. Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

Antibodies of the invention typically bind to their designated target with an affinity constant of at least $10^6$, $10^7$, $10^8$, $10^9$, or $10^{10}$ $M^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

The term "symptom" refers to subjective evidence of a disease, such as altered gait, as perceived by a subject. A "sign" refers to objective evidence of a disease as observed by a physician.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor. Statistical significance means $p \leq 0.05$.

Unless otherwise apparent from the context, the term "about" encompasses values within the standard deviation of the mean of a stated value or +/−5% of a stated value, whichever is greater.

The term "9E4 antibody" refers to any antibody in which each of the CDRs is substantially that of 9E4, and thus includes murine, chimeric, veneered, and humanized 9E4. References to other antibodies, such as 5C1, 1H7, 6H7, and 8A5 have corresponding meanings.

Unless otherwise apparent from the context, reference to a range includes any integer within the range.

A treatment regime refers to a combination of parameters characterizing administration of an immunotherapeutic agent including any or all of dose, frequency of administration, route of administration, and total duration of administration.

BRIEF DESCRIPTION OF THE SEQUENCES

SEQ ID NO:1 is an m9E4VL variable region.
SEQ ID NO:2 is an 63102889Hu9E4VLFr variable region.
SEQ ID NO:3 is an Hu9E4VLv1 variable region.
SEQ ID NO:4 is an Hu9E4VLv2 (No backmutation) variable region.
SEQ ID NO:5 is an Hu9E4VLv3 variable region.
SEQ ID NO:6 is an m9E4VH variable region.
SEQ ID NO:7 is an 1791009Hu9E4VHFr variable region.
SEQ ID NO:8 is an Hu9E4VHv1 variable region.
SEQ ID NO:9 is an Hu9E4VHv2 variable region.
SEQ ID NO: 10 is an Hu9E4VHv3 variable region.
SEQ ID NO: 11 is an Hu9E4VHv4 (no backmutation) variable region.
SEQ ID NO: 12 is the amino acid sequence of natural human wildtype alpha-synuclein.
SEQ ID NO: 13 is a humanized 9E4 light chain constant region (with R) (common for v1, v2, v3).
SEQ ID NO: 14 is a humanized 9E4 light chain constant region (with R) nucleotide sequence (common for v1, v2, v3).
SEQ ID NO: 15 is an amino acid sequence of an exemplary human IgG1 constant region.
SEQ ID NO: 16 is a nucleic acid sequence encoding an exemplary human IgG1 constant region.
SEQ ID NO: 17 is an Hu9E4VLv1 nucleotide sequence variable region.
SEQ ID NO: 18 is an Hu9E4VLv2 nucleotide sequence (no backmutation) variable region.
SEQ ID NO: 19 is an Hu9E4VLv3 nucleotide sequence variable region.
SEQ ID NO:20 is an Hu9E4VHv1 nucleotide sequence variable region.
SEQ ID NO:21 is an Hu9E4VHv2 nucleotide sequence variable region.
SEQ ID NO:22 is an Hu9E4VHv3 nucleotide sequence variable region.
SEQ ID NO:23 is an Hu9E4VHv4 nucleotide sequence (no backmutation) variable region.
SEQ ID NO:24 is an Hu9E4VL signal peptide (common for v1, v2, v3).
SEQ ID NO:25 is an Hu9E4VL signal peptide nucleotide sequence (common for v1, v2, v3).
SEQ ID NO:26 is an Hu9E4VH signal peptide (common for v1, v2, v3).
SEQ ID NO:27 is an Hu9E4VH signal peptide nucleotide sequence (common for v1, v2, v3, v4).
SEQ ID NO:28 is an Hu9E4VL alternative.
SEQ ID NO:29 is an Hu9E4VH alternative.
SEQ ID NO:30 is an amino acid sequence of an exemplary human kappa light chain constant region.
SEQ ID NO:31 is a humanized 9E4 light chain constant region (without R) nucleotide sequence (common for v1, v2, v3).
SEQ ID NO:32 is a humanized 9E4 light chain version 3 (variable region+constant region with Arginine).
SEQ ID NO:33 is a humanized 9E4 light chain version 3 (variable region+constant region without Arginine).
SEQ ID NO:34 is a humanized 9E4 heavy chain version 3 (variable region+constant region).
SEQ ID NO:35 is a humanized 9E4 heavy chain constant region (G1m3 allotype; BIP version).
SEQ ID NO:36 is a humanized 9E4 heavy chain version 3 (variable region+constant region).
SEQ ID NO:37 is a humanized 9E4 heavy chain version 3 (variable region+alternative constant region G1m3 allotype).
SEQ ID NO:38 is an m5C1 antibody mature heavy chain variable region nucleotide sequence.
SEQ ID NO:39 is an m5C1 antibody heavy chain variable region amino acid sequence.
SEQ ID NO:40 is an m5C1 antibody heavy chain signal peptide nucleotide sequence.
SEQ ID NO:41 is an m5C1 antibody heavy chain signal peptide amino acid sequence.
SEQ ID NO:42 is an m5C1 antibody mature light chain variable region nucleotide sequence.
SEQ ID NO:43 is an m5C1 antibody light chain variable region amino acid sequence.
SEQ ID NO:44 is an m5C1 antibody light chain signal peptide nucleotide sequence.
SEQ ID NO:45 is an m5C1 antibody light chain signal peptide amino acid sequence.
SEQ ID NO:46 is a 5C1 immunogen.
SEQ ID NO:47 is an m5C1 heavy chain CDR1.

SEQ ID NO:48 is an m5C1 heavy chain CDR2.
SEQ ID NO:49 is an m5C1 heavy chain CDR3.
SEQ ID NO:50 is an m5C1 light chain CDR1.
SEQ ID NO:51 is an m5C1 light chain CDR2.
SEQ ID NO:52 is an m5C1 light chain CDR3.
SEQ ID NO:53 is a murine 5C1 heavy chain variable region nucleotide sequence with sequence encoding signal peptide.
SEQ ID NO:54 is a murine 5C1 heavy chain variable region sequence with signal peptide.
SEQ ID NO:55 is a murine 5C1 light chain variable region nucleotide sequence with sequence encoding signal peptide.
SEQ ID NO:56 is a murine 5C1 light chain variable region sequence with signal peptide.
SEQ ID NO:57 is a human VH Acceptor FR (Acc #AAY42876.1).
SEQ ID NO:58 is a humanized 5C1H1.
SEQ ID NO:59 is a humanized 5C1H2.
SEQ ID NO:60 is a humanized 5C1H3.
SEQ ID NO:61 is a humanized 5C1H4.
SEQ ID NO:62 is a humanized 5C1H5.
SEQ ID NO:63 is a nucleic acid sequence encoding humanized 5C1 H1.
SEQ ID NO:64 is a nucleic acid sequence encoding humanized 5C1 H2.
SEQ ID NO:65 is a nucleic acid sequence encoding humanized 5C1H3.
SEQ ID NO:66 is a nucleic acid sequence encoding humanized 5C1 H4.
SEQ ID NO:67 is a nucleic acid sequence encoding humanized 5C1H5.
SEQ ID NO:68 is a human VL Acceptor FR (Acc #CAB51293.1).
SEQ ID NO:69 is a humanized 5C1L1.
SEQ ID NO:70 is a humanized 5C1L2.
SEQ ID NO:71 is a humanized 5C1L3.
SEQ ID NO:72 is a humanized 5C1L4.
SEQ ID NO:73 is a nucleic acid sequence encoding humanized 5C1 L1.
SEQ ID NO:74 is a nucleic acid sequence encoding humanized 5C1 L2.
SEQ ID NO:75 is a nucleic acid sequence encoding humanized 5C1L3.
SEQ ID NO:76 is a nucleic acid sequence encoding humanized 5C1 L4.
SEQ ID NO:77 is a nucleic acid sequence encoding an exemplary human kappa light chain constant region.
SEQ ID NO:78 is a non-amyloid component (NAC) domain of alpha-synuclein as reported by Jensen et al.
SEQ ID NO:79 is a non-amyloid component (NAC) domain of alpha-synuclein as reported by Uéda et al.
SEQ ID NO:80 is an m1H7 antibody heavy chain variable nucleotide sequence.
SEQ ID NO:81 is an m1H7 antibody heavy chain variable amino acid sequence.
SEQ ID NO:82 is an m1H7 antibody light chain variable nucleotide sequence.
SEQ ID NO:83 is an m1H7 antibody light chain variable amino acid sequence.
SEQ ID NO:84 is a mature m1H7 antibody heavy chain variable nucleotide sequence.
SEQ ID NO:85 is a mature m1H7 antibody heavy chain variable amino acid sequence.
SEQ ID NO:86 is a mature m1H7 antibody light chain variable nucleotide sequence.
SEQ ID NO:87 is a mature m1H7 antibody light chain variable amino acid sequence.
SEQ ID NO:88 is an m1H7 antibody heavy chain CDR1 (Kabat definition).
SEQ ID NO:89 is an m1H7 antibody heavy chain CDR2 (Kabat definition).
SEQ ID NO:90 is an m1H7 antibody heavy chain CDR3 (Kabat definition).
SEQ ID NO:91 is an m1H7 antibody light chain CDR1 (Kabat definition).
SEQ ID NO:92 is an m1H7 antibody light chain CDR2 (Kabat definition).
SEQ ID NO:93 is an m1H7 antibody light chain CDR3 (Kabat definition).
SEQ ID NO:94 is an Hu1H7VHv1 nucleotide sequence.
SEQ ID NO:95 is an Hu1H7VHv1 amino acid sequence.
SEQ ID NO:96 is an Hu1H7VHv2 nucleotide sequence.
SEQ ID NO:97 is an Hu1H7VHv2 amino acid sequence.
SEQ ID NO:98 is an Hu1H7VHv3 nucleotide sequence.
SEQ ID NO:99 is an Hu1H7VHv3 amino acid sequence.
SEQ ID NO:100 is an Hu1H7VHv4 nucleotide sequence.
SEQ ID NO:101 is an Hu1H7VHv4 amino acid sequence.
SEQ ID NO: 102 is an Hu1H7VHv5 nucleotide sequence.
SEQ ID NO:103 is an Hu1H7VHv5 amino acid sequence.
SEQ ID NO:104 is an Hu1H7VH signal peptide nucleotide sequence.
SEQ ID NO: 105 is an Hu1H7VH signal peptide amino acid sequence.
SEQ ID NO: 106 is an Hu1H7VH signal peptide nucleotide sequence.
SEQ ID NO: 107 is an Hu1H7VH signal peptide amino acid sequence.
SEQ ID NO:108 is an Hu1H7VLv1 nucleotide sequence.
SEQ ID NO: 109 is an Hu1H7VLv1 amino acid sequence.
SEQ ID NO:110 is an Hu1H7VLv2 nucleotide sequence.
SEQ ID NO:111 is an Hu1H7VLv2 amino acid sequence.
SEQ ID NO:112 is an Hu1H7VLv3 nucleotide sequence.
SEQ ID NO: 113 is an Hu1H7VLv3 amino acid sequence.
SEQ ID NO: 114 is an Hu1H7VLv4 nucleotide sequence.
SEQ ID NO:115 is an Hu1H7VLv4 amino acid sequence.
SEQ ID NO: 116 is an Hu1H7VL signal peptide nucleotide sequence.
SEQ ID NO: 117 is an amino acid sequence of BAC02037 (GI-21670055) human acceptor used for heavy chain framework.
SEQ ID NO: 118 is an amino acid sequence of AAY33358 GI-63102905) human acceptor used for light chain framework.
SEQ ID NO: 119 is an Hu1H7VH with no backmutation or CDR mutation.
SEQ ID NO: 120 is an Hu1H7VL with no backmutation or CDR mutation.
SEQ ID NO: 121 is an Hu1H7VH alternative.
SEQ ID NO: 122 is an Hu1H7VL alternative.
SEQ ID NO:123 is an Hu1H7VH CDR3 alternative.
SEQ ID NO: 124 is a humanized 1H7 light chain version 3 (variable region+constant region with Arginine).
SEQ ID NO: 125 is a humanized 1H7 light chain version 3 (variable region+constant region without Arginine).
SEQ ID NO: 126 is a humanized 1H7 heavy chain version 3 (variable region+constant region).
SEQ ID NO: 127 is a humanized 1H7 heavy chain version 3 (variable region+constant region G1m3 allotype).
SEQ ID NO:128 is a humanized 1H7 heavy chain constant region (IgG2).
SEQ ID NO:129 is a humanized 1H7 heavy chain constant region (G1m1 allotype).

DETAILED DESCRIPTION

I. General

The invention provides methods of monitoring immunotherapy directed against alpha-synuclein by comparing a subject's constipation symptoms before treatment and at one or more times during and/or after treatment. An improvement in constipation symptoms during or following treatment provides an indication that the immunotherapy regime is achieving a positive (i.e., desired) outcome. Accordingly, the regime can be continued, or in some cases adjusted to a reduced dose or frequency of administration of the same immunotherapy agent. Conversely, no improvement or worsening of the constipation symptoms provides an indication that the treatment regime is not achieving a positive outcome. Accordingly, the dosage or frequency of administration of the immunotherapy agent can be increased. Alternatively, a treatment regime with a different agent, either another immunotherapy agent, or otherwise can tried.

II. Target Molecule

Natural human wild type alpha-synuclein is a peptide of 140 amino acids having the following amino acid sequence:
MDVFMKGLSK AKEGVVAAAE KTKQGVAEAA GKTKEGVLYV GSKTKEGVVH
GVATVAEKTK EQVTNVGGAV VTGVTAVAQK TVEGAGSIAA ATGFVKKDQL
GKNEEGAPQE GILEDMPVDP DNEAYEMPSE EGYQDYEPEA (SEQ ID NO:12) (Ueda et al., Proc. Natl. Acad. Sci. USA (1993) 90:11282-6); GenBank accession number: P37840. The protein has three recognized domains: an-N-terminal KTKE repeat domain covering amino acids 1-61; a NAC (Non-amyloid component) domain running from about amino acids 60-95; and a C-terminal acidic domain running from about amino acid 98 to 140.

Unless otherwise apparent from the context, reference to alpha-synuclein or its fragments includes the natural human wildtype amino acid sequences indicated above, and human allelic variants thereof, particularly those associated with Lewy body disease (e.g., variants E46K, A30P and A53T, with the first letter indicating the amino acid in SEQ ID NO: 12, the number indicating the codon position in SEQ ID NO: 12, and the second letter indicating the amino acid in the allelic variant). Such variants can optionally be present individually or in any combination in any of the aspects of the invention described below.

III. Lewy Body Diseases

Lewy Body Diseases (LBD) are characterized by degeneration of the dopaminergic system, motor alterations, cognitive impairment, and formation of Lewy bodies (LBs). (McKeith et al., Neurology (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease), Dementia with Lewy Bodies (DLB) (also known as Diffuse Lewy Body Disease (DLBD)), Lewy Body variant of Alzheimer's disease (LBV), Combined Alzheimer's and Parkinson disease, and multiple system atrophy (MSA; e.g., Olivopontocerebellar Atrophy, Striatonigral Degeneration, and Shy-Drager Syndrome). LBD shares symptoms of both Alzheimer's and Parkinson's disease. LBD differs from Parkinson's disease mainly in the location of Lewy Bodies. In LBD, Lewy Bodies form mainly in the cortex. In Parkinson's disease, they form mainly in the substantia nigra. Other Lewy Body diseases include Pure Autonomic Failure, Lewy Body dysphagia, Incidental LBD, and Inherited LBD (e.g., mutations of the alpha-synuclein gene, PARK3 and PARK4).

IV. Immunotherapy Agents

Passive immunotherapy involves treatment with an antibody against alpha-synuclein. Active immunotherapy involves treatment with an agent that induces such an antibody.

1. Antibodies

A. Binding Specificity and Functional Properties

Immunotherapy agents include antibodies specifically binding to the N-terminal, NAC or C-terminal domain of human alpha-synuclein. Some antibodies bind to an epitope within residues 1-10, 91-99, 118-126 or 130-140 of human alpha-synuclein. Antibodies can be monoclonal or polyclonal. A polyclonal serum can be specific to an epitope or range of amino acids within alpha-synuclein in that it lacks antibodies binding outside the epitope or range. Antibodies can be non-human, chimeric, veneered, humanized, or human among other possibilities.

Some antibodies are bispecific, one arm of which is an antibody against alpha synculcin and the other arm of which is an antibody that binds to a receptor expressed on the blood brain barrier, such as an insulin receptor, an insulin-like growth factor (IGF) receptor, a leptin receptor, or a lipoprotein receptor, or preferably a transferrin receptor (Friden et al., PNAS 88:4771-4775, 1991; Friden et al., Science 259: 373-377, 1993). Such a bispecific antibody can be transferred cross the blood brain barrier by receptor-mediated transcytosis. Brain uptake of the bispecific antibody can be further enhanced by engineering the bispecific antibody to reduce its affinity to the blood brain barrier receptor. Reduced affinity for the receptor resulted in a broader distribution in the brain (see, e.g., Atwal. et al. *Sci. Trans. Med.* 3, 84ra43, 2011; Yu et al. *Sci. Trans. Med.* 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star). Fc-engineered IgG1 (Xencor) or DuoBody (based on Fab arm exchange, Genmab).

One exemplary antibody which binds to an epitope with residues 1-10 of alpha-synuclein is mAb 6H7. The cell line designated JH17.6H7.1.54.28 producing the antibody 6H7 has the ATCC accession number PTA-6910 having been deposited under the provisions of the Budapest Treaty with the American Type Culture Collection (ATCC, P.O. Box 1549, Manassas, Va. 20108) on Aug. 4, 2005.

Another exemplary antibody which binds to an epitope within residues 130-140 of alpha-synuclein is mAb 8A5.

The cell line designated JH4.8A5.25.7.36 producing the antibody 8A5 has the ATCC accession number PTA-6909 having been deposited on Aug. 4, 2005.

Another exemplary antibody is mAb 9E4, which binds to an epitope within residues 118-126 of human alpha-synuclein. The cell line designated JH17.9E4.3.37.1.14.2 producing the antibody 9E4 has the ATCC accession number PTA-8221 having been deposited under the provisions of the Budapest Treaty with the American Type Culture Collection (ATCC, P.O. Box 1549, Manassas. Va. 20108) on Feb. 26, 2007. The murine light and heavy chain variable sequences are SEQ ID NO:1 and SEQ ID NO:6, respectively.

Another exemplary antibody is mAb 5C1. The murine light and heavy chain variable sequences are SEQ ID NO:43 and SEQ ID NO:39, respectively.

Another exemplary antibody is mAb 1H7. The cell line designated JH17.1H7.4.24.34 producing the antibody 1H7 has the ATCC accession number PTA-8220 having been deposited under the provisions of the Budapest Treaty with the American Type Culture Collection (ATCC, P.O. Box 1549, Manassas, Va. 20108) on Feb. 26, 2007. The murine light and heavy chain variable sequences are SEQ ID NO:87 and SEQ ID NO:85, respectively.

Such antibodies are described in WO 06/020581 and U.S. Application No. 61/591,835, 61/711,207, 13/750,983, 61/711,204, 61/719,281, 61/840,432, 61/872,366, Ser. No. 14/049,169, 61/553,131, 61/711,204, 61/843,011, and Ser. No. 13/662,261, all of which are incorporated herein by reference for all purposes.

B. Humanized Antibodies

A humanized antibody is a genetically engineered antibody in which the CDRs from a non-human "donor" antibody are grafted into human "acceptor" antibody sequences (see, e.g., Queen et al., U.S. Pat. Nos. 5,530,101 and 5,585,089; Winter et al., U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody variable region sequence, a composite of such sequences, a consensus sequence of human antibody sequences (e.g., light and heavy chain variable region consensus sequences of Kabat, 1991, supra), or a germline variable region sequence. Thus, a humanized antibody of the invention includes antibodies having three light chain and three heavy chain CDRs as defined by Kabat entirely or substantially from a murine antibody, such as 9E4, 5C1, 1H7, 6H7, or 8A5 (donor antibody) and mature variable region framework sequences and constant regions, if present, entirely or substantially from human antibody sequences. Likewise a humanized heavy chain includes heavy chains having three heavy chain CDRs as defined by Kabat from the heavy chain of the donor antibody, and a mature heavy chain variable sequence and heavy chain constant region sequence, if present, entirely or substantially from human antibody heavy chain sequences. Likewise a humanized light chain includes light chains having three light chain CDRs as defined by Kabat from the light chain of the donor antibody, and a mature light chain variable sequence and light chain constant region sequence, if present, entirely or substantially from human antibody light chain sequences. The mature variable region framework sequences of an antibody chain or the constant region sequence of an antibody chain are substantially from a human mature variable region framework sequence or human constant region sequence, respectively, when at least 85%, 90%, 95%, 96%, 97%, 98%, 99% or 100% of corresponding residues defined by Kabat are identical. A CDR is substantially from a corresponding donor CDR if showing at least 85% identity thereto, except in the case of CDRH2 wherein at least 65% identify is required.

Certain amino acids from the human mature variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine mature variable region framework residue and a selected human mature variable region framework residue, the human framework amino acid can be substituted by the equivalent framework amino acid from the mouse antibody when it is reasonably expected that the amino acid:

(1) noncovalently binds antigen directly.
(2) is adjacent to a CDR region,
(3) otherwise interacts with a CDR region (e.g. is within about 6 Å of a CDR region)
(4) mediates interaction between the heavy and light chains.

Exemplary humanized forms of the mouse 9E4 antibody including three exemplified humanized light chain mature variable regions (Hu9E4VLv1-v3; SEQ ID NOs:3-5) and four exemplified humanized heavy chain mature variable regions (Hu9E4VHv1-v4; SEQ ID NOs:8-11).

The exemplary light hand heavy chain mature variable regions can be paired in any combination. A preferred combination is Hu9E4VLv3 (SEQ ID NO:5) and Hu9E4VHv3 (SEQ ID NO:10). An exemplary heavy chain constant region is SEQ ID NO:35. This constant region can be linked to any of the heavy chain variable regions. An exemplary light chain constant region is SEQ ID NO:30. This constant region can be linked to any of the light chain variable regions. A preferred full length heavy chain has the amino acid sequence of SEQ ID NO:37. A preferred full length light chain has the amino acid sequence of SEQ ID NO:32. A preferred combination is an antibody comprising SEQ ID NO:37 and SEQ ID NO:32. The nucleic acids encoding the various heavy and light chains just described are provided in SEQ ID NOS: 17-23.

Exemplary humanized forms of the mouse 1H7 antibody include four exemplified humanized light chain mature variable regions (Hu1H7VLv1-v4; SEQ ID NOs: 108-113) and five exemplified humanized heavy chain mature variable regions (Hu1H7VHv1-v5; SEQ ID NOs:94-103). The exemplary light hand heavy chain mature variable regions can be paired in any combination. A preferred combination is Hu1H7VHv3 (SEQ ID NO:99) and Hu1H7VLv3 (SEQ ID NO: 113). An exemplary heavy chain constant region is SEQ ID NO:35. This constant region can be linked to any of the heavy chain variable regions. An exemplary light chain constant region is SEQ ID NO:30. This constant region can be linked to any of the light chain variable regions. A preferred full length heavy chain has the amino acid sequence of SEQ ID NO: 127 (with the G1m3). A preferred full length light chain has the amino acid sequence of SEQ ID NO: 125 (without Arginine). A preferred combination is an antibody comprising SEQ ID NO: 127 and SEQ ID NO: 125. The nucleic acids encoding the various heavy and light chains just described are provided in SEQ ID NOS. Such humanized antibodies are described in WO 06/020581 and U.S. Ser. Nos. 13/750,983, 14/049,169, 13/662,261, and 61/843,011.

In these or other antibodies described herein, one or more terminal residues can be cleaved in the course of posttranslational processing, particularly for terminal lysines of heavy chain constant regions.

C. Chimeric and Veneered Antibodies

The invention further provides chimeric and veneered forms of non-human antibodies, particularly 9E4, 5C1, 1H7, 6H7, or 8A5.

A chimeric antibody is an antibody in which the mature variable regions of light and heavy chains of a non-human antibody (e.g., a mouse) are combined with light and heavy chain constant regions from an antibody of a different species. Typically, the light and heavy chain constant regions are of human origin, but the constant regions can originate from a different non-human species, such as a rat, as needed (e.g., to facilitate testing of the non-human antibody in an appropriate animal model). Such antibodies substantially or entirely retain the binding specificity of the non-human (e.g., mouse) antibody supplying the variable regions, and are about two-thirds human (or different non-human species) sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of 9E4 are included in the invention.

D. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. An exemplary human light chain kappa constant region has the amino acid sequence of SEQ ID NO: 13. Some such light chain kappa constant regions can be encoded by a nucleic acid sequence. The N-terminal arginine of SEQ ID NO: 13 can be omitted, in which case light chain kappa constant region has the amino acid sequence of SEQ ID NO:30. Some such light chain kappa constant regions can be encoded by a nucleic acid sequence. An exemplary human IgG1 heavy chain constant region has the amino acid sequence of SEQ ID NO: 15 (with or without the C-terminal lysine) or the heavy chain constant region component of SEQ ID NO:37. Some such heavy chain constant regions can be encoded by a nucleic acid sequence. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence encoding a constant region of SEQ ID NO:37. Yet another heavy chain constant region has the amino acid sequence encoding a content region of SEQ ID NO:37 except that it lacks the C-terminal lysine.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597, and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821).

E. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

*E. coli* is a prokaryotic host particularly useful for expressing antibodies, particularly antibody fragments. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibodyproducing myelomas including Sp2/0 and NS0. It can be advantageous to use nonhuman cells. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., *J. Immunol.* 148:1149 (1992).

Having introduced vector(s) encoding antibody heavy and light chains into cell culture, cell pools can be screened for growth productivity and product quality in serum-free media. Top-producing cell pools can then be subjected to FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carbohydrate-oligosaccharide mapping, mass spectrometer, and binning assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, *Protein Purification* (Springer-Verlag, NY, 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO02009/027471, and U.S. Pat. No. 5,888,809).

2. Active Immunotherapy

Immunotherapeutic agents for active immunotherapy induce antibodies against alpha-synuclein. Preferred agents are the alpha-SN peptide itself and fragments thereof. Active agents can be used in combination with an adjuvant or carrier (e.g., a peptide of any length) to help elicit antibodies. US20060259986A1 and WO 05/013889 disclose alpha-synuclein fragments useful as immunotherapeutic agent in methods of treatment of Lewy body disease. Optionally, these fragments can be used in combination with an adjuvant. Optionally the immunotherapeutic agent has 5-20 amino acids of human alpha-synuclein and induces antibodies binding to an epitope within residues 1-10, 91-99, 118-126 or 130-140. Some such immunotherapy agents have 5-5, 5-8, 5-9 or 5-10 amino acids.

Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine (Pam$_3$Cys), mannan (a manose polymer), or glucan (a beta 1→2 polymer)), cytokines (e.g., IL-1, IL-1 alpha and beta peptides, IL-2, gamma-INF, IL-10, GM-CSF), and chemokines (e.g., MIP1alpha and beta, and RANTES). Immunogenic agents can also be linked to peptides that enhance transport across tissues, as described in O'Mahony, WO 97/17613 and WO 97/17614. Immunogens may be linked to the carries with or without spacers amino acids (e.g., gly-gly).

Some conjugates can be formed by linking agents of the invention to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, *Chlamydia trachomitis* major outer membrane protein, diphtheria toxoid, *Plasmodium falciparum* circumsporozite T, *Plasmodium falciparum* CS antigen, *Schistosoma mansoni* triose phosphate isomersae, *Escherichia coli* TraT, and Influenza virus hemagluttinin (HA). The immunogenic peptides of the invention can also be conjugated to the T-cell epitopes described in Sinigaglia et al., Nature, 336:778-780 (1988); Chicz et al., J. Exp. Med., 178:27-47 (1993); Hammer et al., Cell 74:197-203 (1993); Falk et al., Immunogenetics, 39:230-242 (1994); WO 98/23635; and, Southwood et al. J. Immunology, 160:3363-3373 (1998) (each of which is incorporated herein by reference for all purposes).

Alternatively, the conjugates can be formed by linking agents of the invention to at least one artificial T-cell epitope capable of binding a large proportion of MHC Class 11 molecules, such as the pan DR epitope ("PADRE"). PADRE is described in U.S. Pat. No. 5,736,142, WO 95/07707, and Alexander J et al., Immunity, 1:751-761 (1994) (each of which is incorporated herein by reference for all purposes). A preferred PADRE peptide is AKXVAAWTLKAAA (SEQ ID NO: 12), (common residues bolded) wherein X is preferably cyclohexylalanine, tyrosine or phenylalanine, with cyclohexylalanine being most preferred.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the $T_h$ epitope and the peptide immunogen of the invention. In addition to physically separating the $T_h$ epitope from the B cell epitope (i.e., the peptide immunogen), the glycine residues can disrupt any artificial secondary structures created by the joining of the $T_h$ epitope with the peptide immunogen, and thereby eliminate interference between the T and/or B cell responses. The conformational separation between the helper epitope and the antibody eliciting domain thus permits more efficient interactions between the presented immunogen and the appropriate $T_h$ and B cells.

To enhance the induction of T cell immunity in a large percentage of subjects displaying various HLA types to an agent of the present invention, a mixture of conjugates with different $T_h$ cell epitopes can be prepared. The mixture may contain a mixture of at least two conjugates with different $T_h$ cell epitopes, a mixture of at least three conjugates with different $T_h$ cell epitopes, or a mixture of at least four conjugates with different $T_h$ cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Some carrier peptides serve to induce a helper T-cell response against the carrier peptide. The induced helper T-cells in turn induce a B-cell response against the immunogenic peptide linked to the carrier peptide.

Some agents of the invention comprise a fusion protein in which an N-terminal fragment of alpha-SN is linked at its C-terminus to a carrier peptide. In such agents, the N-terminal residue of the fragment of alpha-SN constitutes the N-terminal residue of the fusion protein. Accordingly, such fusion proteins are effective in inducing antibodies that bind to an epitope that requires the N-terminal residue of alpha-SN to be in free form. Some agents of the invention comprise a plurality of repeats of NAC linked at the C-terminus to one or more copy of a carrier peptide. Some fusion proteins comprise different segments of alpha-SN in tandem.

A variety of adjuvants can be used in combination with a peptide, such as alpha-SN, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja *Saponaria Molina* tree found in South America (see Kensil et al., in Vaccine Design: The Subunit and Adjuvant Approach (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., N. Engl. J. Med. 336, 86-91 (1997)), pluronic polymers, and killed mycobacteria. Another adjuvant is CpG (WO 98/40100). Alternatively, alpha-SN can be coupled to an adjuvant. However, such coupling should not substantially change the conformation of alpha-SN so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxphosphoryloxy)-ethylamine (MTP-PE), N-acetylglucsaminyl-N-acetylmuramyl-L-A1-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton. Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1, IL-2, IL-4. IL-6. IL-12, 1L13, and IL-15), macrophage colony stimulating factor (M-CSF), granulocyte-macrophage colony stimulating factor (GM-CSF), and tumor necrosis factor (TNF). Another class of adjuvants is glycolipid analogues including N-glycosylamides. N-glycosylureas and N-glycosylcarbamates, each of which is substituted in the sugar residue by an amino acid, as immunomodulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen V. Diagnostic Criteria for Lewy Body Disease The present methods are in general performed on subjects diagnosed with a Lewy body disease by a qualified health practitioner and having constipation, which is or is at least suspected to be, associated with the disease. Such individuals include any who have received a prior prescription for treatment or prophylaxis of a Lewy body disease. Diagnosis of the Lewy body disease is preferably based on art-recognized criteria for possible or probable Lewy body disease, such as those of DSM-V or DSM IV-TR, the Lewy Body dementia association, the Parkinson's disease society and the like. However, diagnosis can also be based on presence of any signs or symptoms of Lewy body disease that lead a treating physician to conclude that a subject's constipation is most likely the result of a Lewy body disease. Exemplary criteria for diagnosing possible or probable PD are shown below.

Group A: resting tremor, bradykinesia, rigidity and asymmetric onset Group B features: suggestive of alternative diagnoses Prominent postural instability in the first 3 years after symptom onset Freezing phenomena in the first 3 years Hallucinations unrelated to medications in the first 3 years Dementia preceding motor symptoms or in the first year Supranuclear gaze palsy (other than restriction of upward gaze) or slowing of vertical saccades Severe symptomatic dysautonomia unrelated to medications Documentation of a condition known to produce parkinsonism and plausibly connected to the subject's symptoms (such as suitably located focal brain lesions or neuroleptic use within the past 6 months).

Criteria for POSSIBLE diagnosis of Parkinson disease:
At least 2 of the 4 features in Group A are present, at least 1 of these is tremor or bradykinesia
and either none of the features in group B is present or symptoms have been present for less than 3 years and none of the features in group B is present to date; and either substantial and sustained response to levodopa or a dopamine agonist has been documented, or the subject has not had an adequate trial of levodopa or dopamine agonist.

Criteria for PROBABLE diagnosis of Parkinson disease:
At least 3 or the 4 features in Group A are present, and none of the features in Group B is present and substantial and sustained response to levodopa or a dopamine agonist has been documented.

Exemplary criteria for diagnosis of Lewy Body dementia are:

The presence of dementia

At least two of three core features:

fluctuating attention and concentration, recurrent well-formed visual hallucinations, and spontaneous parkinsonian motor signs.

Suggestive clinical features include:

Rapid eye movement (REM) sleep behavior disorder

Severe neuroleptic sensitivity

Low dopamine transporter uptake in basal ganglia demonstrated by SPECT or

PET imaging

In the absence of two core features, the diagnosis of probable DLB can also be made if dementia plus at least one suggestive feature is present with one core feature.

Possible DLB can be diagnosed with the presence of dementia plus one core or suggestive feature.

Early warning signs of Lewy Body disease include for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/gain). Genetic markers of risk toward PD include mutations in the alpha-synuclein or Parkin, UCHLI, and CYP2D6 genes; particularly mutations at positions 30 and 53 of the alpha-synuclein gene. None of these genetics markers or early warning sign is itself diagnostic of a Lewy body disease but they can individually or in combination contribute to a diagnosis of a Lewy body disease.

VI. Determining Constipation Symptoms

As a simple approximation, fewer than three bowel movements per week can be considered constipated, and three or more normal, but more accurate assessment of human symptoms of constipation can be determined by subjects' responses to a questionnaire, of which many are available in the published literature and in medical use One example of such a questionnaire is the PATIENT ASSESSMENT OF CONSTIPATION SYMPTOMS (PAC-SYM). PAC-SYM assesses symptom frequency and severity of chronic constipation (Scand J Gastroenterol 1999; 34: 870-7). This 12-item self-report measure is divided into three symptom subscales (i.e. abdominal, rectal and stool). Items are scored on a four-point Likert scale, with 4 indicating the worst symptom severity. A total score for the PAC-SYM can range from 0 to 48.

The Constipation Scoring System (CSS) (Dis Colon Rectum 1996; 39: 681-5) is an eight-item self-report measure designed to assess the prevalence and severity of constipation. The scoring system is based on eight variables (frequency of bowel movements; difficult or painful evacuation; completeness of evacuation; abdominal pain; time per attempt; type of assistance including laxatives; digitations or enemas; number of unsuccessful attempts at evacuation in a 24-h period and duration of constipation). The CSS consists of seven items that are scored using a five-point Likert scale that ranges from 0 (none of the time) to 4 (all of the time) and one item that is rated on a 0-2 scale. A total score can range from 0 (normal) to 30 (severe constipation). A cut-off score of 15 suggests constipation.

The Knowles Eccersley Scott Symptom (KESS) (Dis Colon Rectum 2000; 43: 1419-26) is an 11-item measure that was developed to help diagnose constipation and to discriminate among pathophysiological subgroups The KESS uses four- to five-point Likert scales that are scored on an unweighted linear integer scale. Total scores can range from 0 (no symptoms) to 39 (high symptom severity). A cut-off score of ≥11 indicates constipation.

The Garrigues Questionnaire (GQ) (Am J Epidemiol 2004; 159: 520-6) is a 21-item self-report measure that was developed to define the presence of chronic constipation. Only 13 of the 21 items are related to bowel habits. The items are scored using two different four-point Likert scales. The first consisted of 'never', 'sometimes' (<25% of the time), 'often' (≥25% of the time) and 'always'. The second consisted of 'never', 'fewer than once a week', 'one or more times a week' and 'every day'.

Constipation in an animal model can be assessed by monitoring frequency and durations of defecations in animal models and/or stool consistency among other measurements.

Subject symptom(s) of constipation can be assessed at least once before commencing immunotherapy to determine a base line reading. Subject symptom(s) of constipation can also assessed at least once after administering an immunotherapy agent. Symptom(s) can be assessed several times both during and after such a regime. For example, symptom(s) can be assessed at a fixed interval after each administration of immunotherapy agent in such a regime.

As is evident from the discussion of questionnaires, subject responses to a questionnaire can be compiled into one or more numerical values providing an overall assessment of the subjects' condition and allowing simple comparison between questionnaires administered at different times to indicate whether symptoms of constipation are improving, staying the same or deteriorating.

VII. Animal Models

The present methods are also useful for evaluating immunotherapeutic agents and regimes in animal models of Lewy body disease, particularly rodents, insects or nonhuman primates. A preferred form of animal model is a transgenic mouse expressing an alpha-synuclein transgene (see Masliah, 2000, Science 287:1265-69) disposed to develop one or more signs or symptoms of Lewy body disease. Similar mice also including an APP transgene can also be used. Another model incorporating a genomic alpha-synuclein transgene with E46K and Rep1 mutations is described in U.S. Pat. No. 8,502,016. Transgenic *Drosophila* expressing human alpha-synuclein are reported by Feany et al., Nature. 2000 Mar. 23; 404(6776):394-8. Other transgenic animal models of Lewy body disease are reviewed by Esbach et al., Neurodegener Dis. 2013 Sep. 24 (eprint).

Animal models can be used for screening immunotherapeutic agents and regimes. An immunotherapeutic agent is administered to an animal model in a regime and one or more symptoms of constipation can be assessed before and after the administration. Other signs and symptoms of Lewy Body disease may or may not also be assessed. An improvement in the one or more symptoms of constipation responsive to administration of the immunotherapeutic agent provides an indication that the immunotherapeutic agent and the regime with which it is administered are useful for treatment of Lewy body disease. Improvement can also be assessed relative to a similar animal model that does not receive the immunotherapeutic agent being tested. Preferably a comparison is performed between populations of the animal model receiving and not receiving the immunotherapeutic agent to determine whether the immunotherapeutic agent and the regime with which it is administered achieves a statistically significant reduction in symptoms of constipation.

VIII. Monitoring and Adjusting Immunotherapy Based on Constipation Symptoms

The methods are practiced on subjects that have been diagnosed with a Lewy body disease including symptoms of constipation. Subjects can be evaluated to establish a baseline for constipation symptoms before commencing immunotherapy. Preferably subjects are evaluated on multiple occasions to establish both a base line and measure of random variation independent of treatment. An immunotherapy agent is then administered in a first regime.

The regime typically includes multiple administrations of the immunotherapy agent over a total period ranging from e.g., a month to five years, and preferably from 1-24 or 6-18 months). One or more constipation symptoms are evaluated at least once during or after the regime. Preferably the symptoms are evaluated on multiple occasions both to establish a measure of random variation and to show a trend in response to immunotherapy. The various assessments of constipation symptoms are then compared. If only two assessments are made, a direct comparison can be made between the two assessments to determine whether the constipation symptoms improved, deteriorated or remained the same between the two assessments. If more than two measurements are made, the measurements can be analyzed as a time course starting before immunotherapy and proceeding through immunotherapy. The analysis again indicates whether constipation symptom(s) improved, deteriorated or remained the same in response to immunotherapy. Comparisons can be performed in a suitably programmed computer, which can also be programmed to provide output as discussed further below. Additionally or alternatively, a frequency of bowel movements of three or more per week after initiating treatment can be considered as a simple indication of a positive response to treatment.

Depending on the outcome of the comparison of one or more constipation symptoms, different subjects may receive different subsequent treatment regimes. In subjects in whom the one or more symptoms improved, it can be concluded that the first regime was successful. Such subjects thereafter receive a second regime, which can be the same as the first regime (because it was successful) or can involve continued administration of the same immunotherapeutic agent as in the first regime but at reduced dosage or frequency (e.g., transition from an induction regime to a maintenance regime). For example, in the second regime, the dose or frequency can be reduced by a factor of at least 1.5, at least 2 or 1.5-5. For purposes of adjusting dosages down, dosages can be classified in four bands (among other possibilities) such as 0.3-1 mg/kg, 1-3 mg/kg, 3-10 mg/kg and 10-30 mg/kg with a downward adjustment changing the dose from being within a higher band to a lower band. The lower band can be any of the bands lower than the initial dose. For example, the dose can be adjusted from a higher band to the next lower band, such as from 3-10 mg/kg to 1-3 mg/kg. The dosages can also be adjusted among exemplary dosages of 0.3, 1, 3, 10 and 30 mg/kg For example, an initial dosage of 30 mg/kg can be adjusted down to any of the other dosages mentioned. In some such methods, dosages at the higher end of those mentioned e.g., 3 mg/kg, 10 mg/kg or 30 mg/kg are used for induction and dosages at the lower end e.g., 0.3 mg/kg, 1 mg/kg or 3 mg/kg used for maintenance. In subjects in whom the one or more symptoms deteriorated or remained the same, it can be concluded that the first regime was unsuccessful or at least less than optimally successful. Such subjects thereafter can receive a third regime, different than the first regime, and second regime. The third regime can involve administering the same immunotherapeutic agent as in the first regime but at an increased dose and frequency. For example, the dose or frequency can be increased by at least a factor of 1.5, at least 2 or 1.5-5. As an example, the dose can be adjusted from being within a lower to a higher band of those mentioned above, or a lower to a higher exemplary dosage. The third regime can also include administering a different agent than the first regime, either a different immunotherapeutic agent (e.g., a different antibody to alpha-synuclein) or a non-immunotherapeutic agent indicated for treatment of a Lewy body disease.

Reference to an improvement or deterioration in symptoms means an improvement which in the physician's judgment is more likely than not due to the treatment rather than random variation in the subject's condition, and is preferably demonstrated by an improvement beyond at least one and preferably two standard deviations of such fluctuation.

Assessment of symptoms of constipation can be made in conjunction with assessing other signs and symptoms of Lewy body disease. Signs of Lewy body disease include accumulation of axonal or neuritic alpha-synuclein aggregates or Lewy bodies in the brain, accumulation of alpha-synuclein in the CSF or body fluids, neuritic dystrophy and reduced synaptic density. An index of changes in synaptic or dentritic density can be measured by markers of synapse formation (synaptophysin) and/or dendrites (MAP2). Symptoms of Lewy body disease include any listed in above under diagnosis. Preferred symptoms for assessment include motor and cognitive functions. In some subjects, improvements in constipation symptoms occur before improvements in one or more, or all of such other symptoms. e.g., reduction of neuritic and/or axonal alpha-synuclein aggregates improving cognitive function, and/or reversing, treating or preventing cognitive decline) in the subject.

The method can be for approved immunotherapeutic agents or as part of a clinical or preclinical trial of an immunotherapeutic agent. The methods can be practiced on a single individual or a population of individuals. If a population, then the population is preferably sufficiently large as to include at least one individual whose symptoms of constipation decrease in response to treatment and at least one individual whose symptoms remain the same or get worse after treatment. The population preferably includes at least 2, 5, 10, 50, 100 or 1000 subjects.

IX. Treating Constipation

The invention further provides methods of treating constipation in subjects diagnosed with a Lewy body disease and having symptoms of constipation suspected of being due to the Lewy body disease. Such methods involve administering an effective regime of an immunotherapeutic agent against alpha-synuclein to a subject such as to improve one or more symptoms of constipation in the subject. Preferably one or more symptoms of constipation are monitored before and during treatment to allow assessment of whether the treatment is effective to reduce symptoms of constipation.

X. Therapeutic Regimes

In therapeutic applications, an antibody or agent to induce an antibody is administered to a subject diagnosed a Lewy body disease in a regime (dose, frequency and route of administration) known or suspected to be effective to ameliorate or at least inhibit further deterioration of at least one sign or symptom of the disease. In prophylactic applications, an antibody or agent to induce an antibody is administered to a subject at increased risk of a Lewy body disease but not yet having sufficient symptoms to be diagnosed with the disease in a regime known or suspected to be effective to inhibit or delay onset of at least one sign or symptom of the disease.

A regime is considered therapeutically or prophylactically effective if a more favorable outcome is demonstrated in treated subjects versus control subjects in a controlled animal model or clinical trial (e.g., a phase II, phase II/III or phase III trial) at the p<0.05 or 0.01 or even 0.001 level. However, due to variations in genetics, subject characteristic and environment and disease subtype between individual subjects, a regime that is effective in one subject may not be effective in another subject or may be effective to different extents.

Effective doses vary depending on many different factors, including means of administration, target site, physiological state of the subject including type of Lewy body disease, whether the subject is an ApoE carrier, whether the subject is human or an animal, other medications administered, and whether treatment is prophylactic or therapeutic.

An exemplary dosage range for antibodies is from about 0.1 to 50 mg/kg of subject body weight. An additional exemplary dosage range for antibodies is from about 0.1 to 60 mg/kg of subject body weight. Antibody can be administered such doses daily, on alternative days, weekly, fortnightly, monthly, quarterly, annually or according to any other schedule determined by empirical analysis. An exemplary treatment entails administration in multiple dosages over a prolonged period, for example, of at least six months, and sometimes at least 12 or 18 months. Additional exemplary treatment regimes entail administration once per every two weeks or once a month or once every 3 to 6 months.

Exemplary dosage ranges for an antibody to alpha-synuclein in any of the present methods include 0.3 mg/kg, 1.0 mg/kg, 3.0 mg/kg and 30 mg/kg, or a dose within any of the following ranges 0.3-1.0 mg/kg, 1.0-3.0 mg/kg, 3.0-10 mg/kg or 10-30 mg/kg or within any combination of such ranges (e.g., 0.3 to 3 mg/kg or 0.3 mg/kg). Such dosages can be administered at approximately monthly intervals (e.g., every 28, 29, 30 or 31 days) or by the calendar month. Intervals of a calendar month or 28 days are preferred. An interval of once every 28-31 days means that the dose can be administered once every 28 days, once every 29 days, once every 30 days, once every 31 days, once per calendar month, or any permutation of these intervals (e.g., first interval between doses, 28 days, second interval 29 days, third interval 31 days, fourth interval 38 days). Other regimes delivering the same area under the curve within experimental error can also be used. One example of alpha synuclein antibodies usable by this regime is humanized 9E4, or particularly the H3V3 version in which the light chain variable region is designated SEQ ID NO:5 and heavy chain variable region SEQ ID NO: 10, or more specifically the H3V3 version in which the full-length light chain is designated SEQ ID NO:32 and the full-length heavy chain SEQ ID NO:37.

Antibodies can be administered via a peripheral route (i.e., one in which an administered antibody crosses the blood brain barrier to reach an intended site in the brain. Routes of administration include topical, intravenous, oral, subcutaneous, intraarterial, intracranial, intrathecal, intraperitoneal, intranasal or intramuscular. Some routes for administration of antibodies are intravenous and subcutaneous. This type of injection is most typically performed in the arm or leg muscles. In some methods, agents are injected directly into a particular tissue where deposits have accumulated, for example intracranial injection.

The present regimes can be administered in combination with another agent effective in treatment or prophylaxis of the disease being treated. The other agent can be another immunotherapeutic agent described herein or other agent for treating Parkinson's disease including levodopa, benzaseride, carbidopa, dopamine agonists, non-ergot dopamine agonists, catechol-O-methyl ("COMT") inhibitors such as, for example, entacopone or tolcopone, monoamine oxidase ("MAO") inhibitors, such as, for example, rasagaline, amantadine, or anticholinergic agents can be used in combination with the present regimes.

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank and UniProtKB/Swiss-Prot accession numbers and the like or in website, or disease criteria of an organization, the application refers to those in effect on its effective filing date.

What is claimed is:

1. A method of assessing the efficacy of immunotherapy against alpha-synuclein in subjects diagnosed with a Lewy Body disease and having one or more constipation symptoms, comprising:
   (a) evaluating the subjects' constipation symptoms before administration of an immunotherapeutic agent in a first regime;
   (b) administering the immunotherapeutic agent to the subjects in the first regime;
   (c) evaluating the subjects' constipation symptoms after administering the iummunotherapeutic agent in the first regime,
   (d) comparing the subjects' constipation symptoms before and after administering the immunotherapeutic agent in the first regime;
   (e) administering a second regime to subjects whose symptoms improve and a third regime to subjects whose symptoms deteriorate, the second and third regimes being different.

2. The method of claim 1, wherein the second regime is the same as the first regime.

3. The method of claim 1, wherein the second regime administers the same immunotherapy agent as the first regime at a reduced dosage or frequency.

4. The method of claim 1 or 2, wherein the third regime administers the same immunotherapy agent as the first regime at an increased dosage or frequency.

5. The method of claim 1, wherein the third regime administers a different immunotherapy agent than the first regime, or a non-immunotherapy agent.

6. The method of claim 1, wherein the Lewy body disease is Parkinson's disease.

7. The method of claim 1, wherein the Lewy body disease is dementia with Lewy bodies.

8. The method of claim 1, wherein the immunotherapy agent is an antibody that specifically binds to alpha-synuclein.

9. The method of claim 1, wherein the immunotherapy agent induces an antibody that specifically binds to alpha-synuclein.

10. The method of claim 8 or 9, wherein the antibody binds to an epitope within residues 1-10, 91-99, 118-126 or 130-140 of alpha-synuclein.

11. The method of claim 10, wherein the antibody binds to an epitope within residues 118-126 of alpha-synuclein.

12. The method of claim 1, wherein the immunotherapeutic agent is an antibody comprising the six Kabat CDRs of 9E4, 5C1, 1H7, 6H7, or 8A5.

13. The method of claim 12, wherein the antibody is humanized 9E4 comprising a heavy chain of SEQ ID NO:37 and a light chain of SEQ ID NO:32.

14. The method of claim 1, wherein the subject's constipation symptoms are evaluated from subject answers to a questionnaire.

15. The method of claim 14, wherein the questionnaire is the PAC-SYM questionnaire.

16. The method of claim 1, wherein the subjects' constipation symptoms are evaluated on at least first and second occasions respectively after first and second administrations of the immunotherapy agent in the first regime.

17. The method of claim 1, wherein the dose or frequency is reduced by at least half in the second regime relative to the first regime.

18. The method of claim 1, wherein the dose or frequency is increased by at least a factor of two in the third regime relative to the second regime.

19. The method of claim 1, further comprising monitoring the subjects for changes in one or more signs or symptoms of the Lewy body disease other than constipation in response to the first regime.

20. The method of claim 19, wherein the signs or symptoms include motor functioning, cognitive function, and level of alpha-synuclein in the brain or body fluid.

21. A method of claim 1, wherein the immunotherapeutic agent is a humanized 9E4 antibody and the dose is 0.3-1.0 mg/kg, 1.0-3.0 mg/kg, 3.0-10 mg/kg or 10-30 mg/kg administered with a frequency of once every 28-31 days, optionally monthly.

22. A method of evaluating an immunotherapy regime comprising
   administering an immunotherapy regime against alpha-synuclein to a transgenic animal model expressing an alpha-synuclein transgene and disposed to develop signs and symptoms of a Lewy body disease; and
   determining one or more symptoms of constipation before and after administering the immunotherapy regime, wherein the monitoring comprises monitoring frequency and duration of defecations and/or stool consistency, an improvement of the symptoms providing an indication that the immunotherapy regime is useful for treating Lewy body disease.

23. The method of claim 22, wherein the immunotherapeutic agent is a humanized 9E4 antibody and the dose is 0.3-1.0 mg/kg, 1.0-3.0 mg/kg, 3.0-10 mg/kg or 10-30 mg/kg administered with a frequency of once every 28-31 days, optionally monthly.

24. A method of assessing the efficacy of immunotherapy against alpha-synuclein in a subject diagnosed with a Lewy Body disease and having one or more constipation symptoms, comprising:
   (a) evaluating the subject's constipation symptoms before administration of an immunotherapeutic agent in a first regime;
   (b) administering the immunotherapeutic agent to the subject in the first regime;
   (c) evaluating the subject's constipation symptoms after administering the immunotherapeutic agent in the first regime, (d) comparing the subject's constipation symptoms before and after administering the immunotherapeutic agent in the first regime; wherein the subject's symptoms improve;
(e) administering a second regime, which is the same as the first regime, or which administers the same immunotherapeutic agent as the first regime at a reduced dose or frequency.

25. The method of claim 24, wherein the immunotherapeutic agent is a humanized 9E4 antibody and the dose is 0.3-1.0 mg/kg, 1.0-3.0 mg/kg, 3.0-10 mg/kg or 10-30 mg/kg administered with a frequency of once every 28-31 days, optionally monthly.

26. A method of assessing the efficacy of immunotherapy against alpha-synuclein in a subject diagnosed with a Lewy Body disease and having one or more constipation symptoms, comprising:
(a) evaluating the subject's constipation symptoms before administration of an immunotherapeutic agent in a first regime;
(b) administering the immunotherapeutic agent to the subject in the first regime;
(c) evaluating the subject's constipation symptoms after administering the immunotherapeutic agent in the first regime,
(d) comparing the subject's constipation symptoms before and after administering the immunotherapeutic agent in the first regime; wherein the subject's symptoms remain the same or deteriorate;
(e) administering a second regime, which administers the same immunotherapeutic agent as the first regime at an increased dose or frequency or which administers a different immunotherapeutic agent or which administers a non-immunotherapeutic agent effective for treatment of Lewy body disease.

27. The method of claim 26, wherein the immunotherapeutic agent is a humanized 9E4 antibody and the dose is 0.3-1.0 mg/kg, 1.0-3.0 mg/kg, 3.0-10 mg/kg or 10-30 mg/kg administered with a frequency of once 28-31 days, optionally monthly.

* * * * *